US006103723A

United States Patent [19]

Bergman et al.

[11] Patent Number: 6,103,723

[45] Date of Patent: Aug. 15, 2000

[54] INHIBITORS OF FARNESYL-PROTEIN TRANSFERASE

[75] Inventors: Jeffrey M. Bergman, Telford; Christopher J. Dinsmore; Samuel L. Graham, both of Schwenksville, all of Pa.

[73] Assignee: Merck & Co., Inc., Rahway, N.J.

[21] Appl. No.: 09/170,951

[22] Filed: Oct. 13, 1998

Related U.S. Application Data

[60] Provisional application No. 60/064,342, Oct. 17, 1997.

[51] Int. Cl.$^{7}$ ...................... A61K 31/504; A61K 31/553; C07D 487/08; C07D 498/08

[52] U.S. Cl. ......................... 514/249; 514/250; 540/456; 540/468; 544/349

[58] Field of Search .................................... 540/456, 468; 544/349; 514/249, 250

[56] References Cited

U.S. PATENT DOCUMENTS

| | | | |
|---|---|---|---|
| 5,756,528 | 5/1998 | Anthony et al. | 514/399 |
| 5,780,488 | 7/1998 | Bergman et al. | 514/357 |
| 5,780,492 | 7/1998 | Dinsmore et al. | 514/397 |

OTHER PUBLICATIONS

Cignarella, et. al, "Bicyclic Homologs of Piperazine. Synthesis of Pharmacologically Active 8–Methyl–3,8–diazabicyclo[3.2.1]octanes. III", Bicyclic Homologs of Piperazine, vol. 6, pp. 29–35, (Jan., 1963).

Cignarella, et. al, "Bicyclic Homologs of Piperazine. V. Synthesis and Analgesic Activity of 3–Methyl–3,8–diazabicyclooctane Derivatives", Bicyclic Homologs of Piperazine, vol. 6, pp. 385–387 (Jul., 1963).

Cignarella, et.al, "Bicyclic Homologs of Piperazine, VI. Synthesis and Analgesic Activity of 3–Substituted 8–Propionyl–3,8–diazabicyclo[3.2.1]octanes", Analgesic Bicyclic Homologs of Piperazine, vol. 6, pp. 764–766 (Nov., 1963).

Gibbs, J.B. et al., "Selective Inhibition of Farnesyl–Protein Transferase Blocks Ras Processing in Vivo," The Journal of Biological Chemistry, vol. 268, No. 11, pp. 7617–7620 (1993).

Goldstein, J.L. et al., "Nonfarnesylated Tetrapeptide Inhibitors of Protein Farnesyltransferase," The Journal of Biological Chemistry, vol. 266, No. 24, pp. 15575–15578 (1991).

Graham, S.L., "Inhibitors of protein farnesylation: a new approach to cancer chemotherapy, " Exp. Opin. Ther. Patents, Vol. 5 (12), pp. 1269–1285 (1995).

Graham, S.L. and Williams, Theresa M., "Inhibitors of protein franesylation," Exp. Opin. Ther. Patents, vol. 6 (12), pp. 1295–1304 (1996).

James, G.L. et al., "Benzodiazepine Peptidomimetic BZA–5B Interrupts the MAP Kinase Activation Pathway in H–Ras–transformed Rat–1 Cells, but Not in Untransformed Cells," The Jour. of Biol. Chem., vol. 269, No. 44, pp. 27705–27714 (1994).

James, G.L., et al., "Polylysine and CVIM Sequences of K–RasB Dictate Specificity of Prenylation and Confer Resistance to Benzodiazepine Peptidomimetic in Vitro", The Jour. of Biol. Chem., vol. 270, No. 11, pp. 6221–6626 (1995).

Kohl, N.E., et al., "Inhibition of farnesyltransferase induces regression of mammary and salivary carcinomas in ras transgenic mice, " Nature Medicine, vol. 1, No. 8, pp. 792–797 (1995).

Kohl, N.E. et al., "Protein farnesyltransferase inhibitors block the growth of ras–dependent tumors in nude mice", Proc. Natl. Acad. Sci. USA, Med. Sciences, vol. 91, pp. 9141–9145 (1994).

Kohl, N.E. et al., "Selective Inhibition of ras–Dependent Transformation by a Farnesyltransferase Inhibitor", Science, vol. 260, pp. 1934–1937 (1993).

Pompliano, D.L., "Steady–State Kinetic Mechanism of Ras Farnesyl:Protein Transferase," Biochemistry, vol. 31, pp. 3800–3807 (1992).

Sepp–Lorenzino, L., et al., "A Peptidomimetic Inhibitor of Farnesyl:Protein Transferase Blocks the Anchorage–dependent and–independent Growth of Human Tumor Cell Lines," Cancer Research, vol. 55, pp. 5302–5309 (1995).

Testa, E., "Omologhi Biciclici Della Piperazina", II Farmaco—Ed. Sc., vol. 24, pp. 418–434 (1968) (This reference is in Italian but the reference itself provides a short English summary of what is disclosed therein.).

*Primary Examiner*—Richard L. Raymond
*Attorney, Agent, or Firm*—Dianne Pecoraro; Mark R. Daniels

[57] ABSTRACT

The present invention is directed to compounds which inhibit farnesyl-protein transferase (FTase) and the farnesylation of the oncogene protein Ras. The invention is further directed to chemotherapeutic compositions containing the compounds of this invention and methods for inhibiting farnesyl-protein transferase and the farnesylation of the oncogene protein Ras.

34 Claims, No Drawings

SEQUENCE LISTING

```
<160> NUMBER OF SEQ ID NOS: 26

<210> SEQ ID NO 1
<211> LENGTH: 4
<212> TYPE: PRT
<213> ORGANISM: Homosapien

<400> SEQUENCE: 1

Cys Val Ile Met
 1


<210> SEQ ID NO 2
<211> LENGTH: 4
<212> TYPE: PRT
<213> ORGANISM: Homosapien

<400> SEQUENCE: 2

Cys Val Leu Leu
 1


<210> SEQ ID NO 3
<211> LENGTH: 4
<212> TYPE: PRT
<213> ORGANISM: Homosapien

<400> SEQUENCE: 3

Cys Val Val Met
 1


<210> SEQ ID NO 4
<211> LENGTH: 4
<212> TYPE: PRT
<213> ORGANISM: Homosapien
```

-continued

<400> SEQUENCE: 4

Cys Ile Ile Met
1

<210> SEQ ID NO 5
<211> LENGTH: 4
<212> TYPE: PRT
<213> ORGANISM: Homosapien

<400> SEQUENCE: 5

Cys Leu Leu Leu
1

<210> SEQ ID NO 6
<211> LENGTH: 4
<212> TYPE: PRT
<213> ORGANISM: Homosapien

<400> SEQUENCE: 6

Cys Gln Leu Leu
1

<210> SEQ ID NO 7
<211> LENGTH: 4
<212> TYPE: PRT
<213> ORGANISM: Homosapien

<400> SEQUENCE: 7

Cys Ser Ile Met
1

<210> SEQ ID NO 8
<211> LENGTH: 4
<212> TYPE: PRT
<213> ORGANISM: Homosapien

<400> SEQUENCE: 8

Cys Ala Ile Met
1

<210> SEQ ID NO 9
<211> LENGTH: 4
<212> TYPE: PRT
<213> ORGANISM: Homosapien

<400> SEQUENCE: 9

Cys Lys Val Leu
1

<210> SEQ ID NO 10
<211> LENGTH: 4
<212> TYPE: PRT
<213> ORGANISM: Homosapien

<400> SEQUENCE: 10

Cys Leu Ile Met
1

<210> SEQ ID NO 11
<211> LENGTH: 4
<212> TYPE: PRT
<213> ORGANISM: Homosapien

<400> SEQUENCE: 11

-continued

```
Cys Val Leu Ser
 1


<210> SEQ ID NO 12
<211> LENGTH: 4
<212> TYPE: PRT
<213> ORGANISM: Homosapien

<400> SEQUENCE: 12

Cys Ala Ile Leu
 1


<210> SEQ ID NO 13
<211> LENGTH: 15
<212> TYPE: PRT
<213> ORGANISM: Homosapien

<400> SEQUENCE: 13

Gly Lys Lys Lys Lys Lys Lys Ser Lys Thr Lys Cys Val Ile Met
 1               5                  10                  15


<210> SEQ ID NO 14
<211> LENGTH: 86
<212> TYPE: DNA
<213> ORGANISM: Artificial Sequence
<220> FEATURE:
<223> OTHER INFORMATION: completely synthesized

<400> SEQUENCE: 14

tctcctcgag gccaccatgg ggagtagcaa gagcaagcct aaggacccca gccagcgccg     60

gatgacagaa tacaagcttg tggtgg                                          86


<210> SEQ ID NO 15
<211> LENGTH: 33
<212> TYPE: DNA
<213> ORGANISM: Artificial Sequence
<220> FEATURE:
<223> OTHER INFORMATION: completely synthesized

<400> SEQUENCE: 15

cacatctaga tcaggacagc acagacttgc agc                                  33


<210> SEQ ID NO 16
<211> LENGTH: 41
<212> TYPE: DNA
<213> ORGANISM: Artificial Sequence
<220> FEATURE:
<223> OTHER INFORMATION: completely synthesized

<400> SEQUENCE: 16

tctcctcgag gccaccatga cagaatacaa gcttgtggtg g                         41


<210> SEQ ID NO 17
<211> LENGTH: 38
<212> TYPE: DNA
<213> ORGANISM: Artificial Sequence
<220> FEATURE:
<223> OTHER INFORMATION: completely synthesized

<400> SEQUENCE: 17

cactctagac tggtgtcaga gcagcacaca cttgcagc                             38


<210> SEQ ID NO 18
<211> LENGTH: 38
<212> TYPE: DNA
```

-continued

<213> ORGANISM: Artificial Sequence
<220> FEATURE:
<223> OTHER INFORMATION: completely synthesized

<400> SEQUENCE: 18
gagagaattc gccaccatga cggaatataa gctggtgg 38

<210> SEQ ID NO 19
<211> LENGTH: 33
<212> TYPE: DNA
<213> ORGANISM: Artificial Sequence
<220> FEATURE:
<223> OTHER INFORMATION: completely synthesized

<400> SEQUENCE: 19
gagagtcgac gcgtcaggag agcacacact tgc 33

<210> SEQ ID NO 20
<211> LENGTH: 22
<212> TYPE: DNA
<213> ORGANISM: Artificial Sequence
<220> FEATURE:
<223> OTHER INFORMATION: completely synthesized

<400> SEQUENCE: 20
ccgccggcct ggaggagtac ag 22

<210> SEQ ID NO 21
<211> LENGTH: 38
<212> TYPE: DNA
<213> ORGANISM: Artificial Sequence
<220> FEATURE:
<223> OTHER INFORMATION: completely synthesized

<400> SEQUENCE: 21
gagagaattc gccaccatga ctgagtacaa actggtgg 38

<210> SEQ ID NO 22
<211> LENGTH: 32
<212> TYPE: DNA
<213> ORGANISM: Artificial Sequence
<220> FEATURE:
<223> OTHER INFORMATION: completely synthesized

<400> SEQUENCE: 22
gagagtcgac ttgttacatc accacacatg gc 32

<210> SEQ ID NO 23
<211> LENGTH: 21
<212> TYPE: DNA
<213> ORGANISM: Artificial Sequence
<220> FEATURE:
<223> OTHER INFORMATION: completely synthesized

<400> SEQUENCE: 23
gttggagcag ttggtgttgg g 21

<210> SEQ ID NO 24
<211> LENGTH: 38
<212> TYPE: DNA
<213> ORGANISM: Artificial Sequence
<220> FEATURE:
<223> OTHER INFORMATION: completely synthesized

<400> SEQUENCE: 24
gagaggtacc gccaccatga ctgaatataa acttgtgg 38

-continued

```
<210> SEQ ID NO 25
<211> LENGTH: 36
<212> TYPE: DNA
<213> ORGANISM: Artificial Sequence
<220> FEATURE:
<223> OTHER INFORMATION: completely synthesized

<400> SEQUENCE: 25

ctctgtcgac gtatttacat aattacacac tttgtc                              36


<210> SEQ ID NO 26
<211> LENGTH: 24
<212> TYPE: DNA
<213> ORGANISM: Artificial Sequence
<220> FEATURE:
<223> OTHER INFORMATION: completely synthesized

<400> SEQUENCE: 26

gtagttggag ctgttggcgt aggc                                           24
```

INHIBITORS OF FARNESYL-PROTEIN TRANSFERASE

DOMESTIC PRIORITY CLAIM

This application claims priority from the U.S. Provisional Application No. 60/064,342, filed Oct. 17, 1997.

BACKGROUND OF THE INVENTION

The Ras proteins (Ha-Ras, Ki4a-Ras, Ki4b-Ras and N-Ras) are part of a signalling pathway that links cell surface growth factor receptors to nuclear signals initiating cellular proliferation. Biological and biochemical studies of Ras action indicate that Ras functions like a G-regulatory protein. In the inactive state, Ras is bound to GDP. Upon growth factor receptor activation Ras is induced to exchange GDP for GTP and undergoes a conformational change. The GTP-bound form of Ras propagates the growth stimulatory signal until the signal is terminated by the intrinsic GTPase activity of Ras, which returns the protein to its inactive GDP bound form (D. R. Lowy and D. M. Willumsen, *Ann. Rev. Biochem.* 62:851–891 (1993)). Mutated ras genes (Ha-ras, Ki4a-ras, Ki4b-ras and N-ras) are found in many human cancers, including colorectal carcinoma, exocrine pancreatic carcinoma, and myeloid leukemias. The protein products of these genes are defective in their GTPase activity and constitutively transmit a growth stimulatory signal.

Ras must be localized to the plasma membrane for both normal and oncogenic functions. At least 3 post-translational modifications are involved with Ras membrane localization, and all 3 modifications occur at the C-terminus of Ras. The Ras C-terminus contains a sequence motif termed a "CAAX" or "Cys-$Aaa^1$-$Aaa^2$-Xaa" box (Cys is cysteine, Aaa is an aliphatic amino acid, the Xaa is any amino acid) (Willumsen et al., *Nature* 310:583–586 (1984)). Depending on the specific sequence, this motif serves as a signal sequence for the enzymes farnesyl-protein transferase or geranylgeranyl-protein transferase, which catalyze the alkylation of the cysteine residue of the CAAX motif with a $C_{15}$ or $C_{20}$ isoprenoid, respectively. (S. Clarke., *Ann. Rev. Biochem.* 61:355–386 (1992); W. R. Schafer and J. Rine, *Ann. Rev. Genetics* 30:209–237 (1992)). The Ras protein is one of several proteins that are known to undergo post-translational farnesylation. Other farnesylated proteins include the Ras-related GTP-binding proteins such as Rho, fungal mating factors, the nuclear lamins, and the gamma subunit of transducin. James, et al., *J. Biol. Chem.* 269, 14182 (1994) have identified a peroxisome associated protein Pxf which is also farnesylated. James, et al., have also suggested that there are farnesylated proteins of unknown structure and function in addition to those listed above.

Inhibition of farnesyl-protein transferase has been shown to block the growth of Ras-transformed cells in soft agar and to modify other aspects of their transformed phenotype. It has also been demonstrated that certain inhibitors of farnesyl-protein transferase selectively block the processing of the Ras oncoprotein intracellularly (N. E. Kohl et al., *Science*, 260:1934–1937 (1993) and G. L. James et al., *Science*, 260:1937–1942 (1993). Recently, it has been shown that an inhibitor of farnesyl-protein transferase blocks the growth of ras-dependent tumors in nude mice (N. E. Kohl et al., *Proc. Natl. Acad. Sci U.S.A.*, 91:9141–9145 (1994) and induces regression of mammary and salivary carcinomas in ras transgenic mice (N. E. Kohl et al., *Nature Medicine*, 1:792–797 (1995).

Indirect inhibition of farnesyl-protein transferase in vivo has been demonstrated with lovastatin (Merck & Co., Rahway, N.J.) and compactin (Hancock et al., ibid; Casey et al., ibid; Schafer et al., *Science* 245:379 (1989)). These drugs inhibit HMG-CoA reductase, the rate limiting enzyme for the production of polyisoprenoids including farnesyl pyrophosphate. Farnesyl-protein transferase utilizes farnesyl pyrophosphate to covalently modify the Cys thiol group of the Ras CAAX box with a farnesyl group (Reiss et al., *Cell*, 62:81–88 (1990); Schaber et al., *J. Biol. Chem.*, 265:14701–14704 (1990); Schafer et al., *Science*, 249:1133–1139 (1990); Manne et al., *Proc. Natl. Acad. Sci USA*, 87:7541–7545 (1990)). Inhibition of farnesyl pyrophosphate biosynthesis by inhibiting HMG-CoA reductase blocks Ras membrane localization in cultured cells. However, direct inhibition of farnesyl-protein transferase would be more specific and attended by fewer side effects than would occur with the required dose of a general inhibitor of isoprene biosynthesis.

Inhibitors of farnesyl-protein transferase (FPTase) have been described in two general classes. The first are analogs of farnesyl diphosphate (FPP), while the second class of inhibitors is related to the protein substrates (e.g., Ras) for the enzyme. The peptide derived inhibitors that have been described are generally cysteine containing molecules that are related to the CAAX motif that is the signal for protein prenylation. (Schaber et al., ibid; Reiss et. al., ibid; Reiss et al., *PNAS*, 88:732–736 (1991)). Such inhibitors may inhibit protein prenylation while serving as alternate substrates for the farnesyl-protein transferase enzyme, or may be purely competitive inhibitors (U.S. Pat. No. 5,141,851, University of Texas; N. E. Kohl et al., *Science*, 260:1934–1937 (1993); Graham, et al., *J. Med. Chem.*, 37, 725 (1994)). In general, deletion of the thiol from a CAAX derivative has been shown to dramatically reduce the inhibitory potency of the compound. However, the thiol group potentially places limitations on the therapeutic application of FPTase inhibitors with respect to pharmacokinetics, pharmacodynamics and toxicity. Therefore, a functional replacement for the thiol is desirable.

It has recently been reported that farnesyl-protein transferase inhibitors are inhibitors of proliferation of vascular smooth muscle cells and are therefore useful in the prevention and therapy of arteriosclerosis and diabetic disturbance of blood vessels (JP H7-112930).

It has recently been disclosed that certain tricyclic compounds which optionally incorporate a piperidine moiety are inhibitors of FPTase (WO 95/10514, WO 95/10515 and WO 95/10516). Imidazole-containing inhibitors of farnesyl protein transferase have also been disclosed (WO 95/09001 and EP 0 675 112 A1).

It is, therefore, an object of this invention to develop confromationally constrained compounds that do not have a thiol moiety, and that will inhibit farnesyl-protein transferase and thus, the post-translational farnesylation of proteins. It is a further object of this invention to develop chemotherapeutic compositions containing the compounds of this invention and methods for producing the compounds of this invention.

SUMMARY OF THE INVENTION

The present invention comprises conformationally constrained compounds that do not resemble peptides and which inhibit the farnesyl-protein transferase. Further contained in this invention are chemotherapeutic compositions containing these farnesyl transferase inhibitors and methods for their production.

The compounds of this invention are illustrated by the formulae A and B:

A

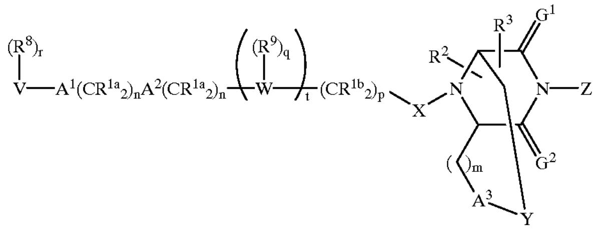

B

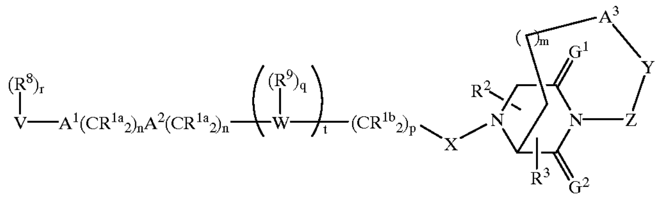

DETAILED DESCRIPTION OF THE INVENTION

The compounds of this invention are useful in the inhibition of farnesyl-protein transferase and the farnesylation of the oncogene protein Ras. In a first embodiment of this invention, the inhibitors of farnesyl-protein transferase are illustrated by the formula A:

A

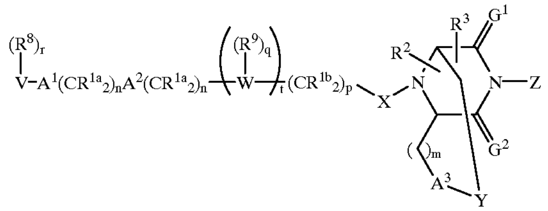

wherein:

$R^{1a}$ and $R^{1b}$ are independently selected from:

a) hydrogen, b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $CN(R^{10})_2NC(O)$—, $(R^{10})_2N$—$C(NR^{10})$—, CN, $NO_2$, $R^{10}C(O)$—, $N_3$, —$N(R^{10})_2$, or $R^{11}OC(O)NR^{10}$—, c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, CN, $(R^{10})_2N$—$C(NR^{10})$—, $R^{10}C(O)$—, $N_3$, —$N(R^{10})_2$, and $R^{11}OC(O)$—$NR^{10}$—;

$R^2$ and $R^3$ are independently selected from: H, unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

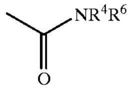 or 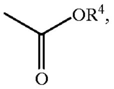

wherein the substituted group is substituted with one or more of:

1) aryl or heterocycle, unsubstituted or substituted with:
   a) $C_{1-4}$ alkyl,
   b) $(CH_2)_pOR^4$,
   c) $(CH_2)_pNR^4R^6$,
   d) halogen,
   e) CN,
2) $C_{3-6}$ cycloalkyl,
3) $OR^4$,
4) $SR^5$, $S(O)R^5$, $SO_2R^5$,
5) —$NR^4R^6$,

6)

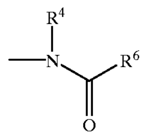

7)

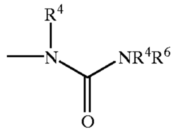

8)

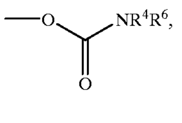

9)

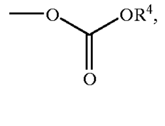

-continued

10)

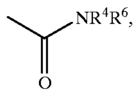

11)

$—SO_2—NR^4R^6$,

12)

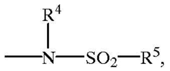

13)

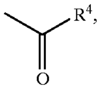

14)

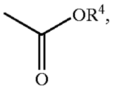

15) $N_3$, or

16) F;

or $R^2$ and $R^3$ are attached to the same C atom and are combined to form $—(CH_2)_u—$ wherein one of the carbon atoms is optionally replaced by a moiety selected from: O, $S(O)_m$, —NC(O)—, and $—N(COR^{10})—$;

and $R^2$ and $R^3$ are optionally attached to the same carbon atom;

$R^4$ and $R^6$ are independently selected from: H, $C_{1-4}$ alkyl, $C_{3-6}$ cycloalkyl, heterocycle, aryl, aroyl, heteroaroyl, arylsulfonyl, heteroarylsulfonyl, unsubstituted or substituted with:

a) $C_{1-4}$ alkoxy, b) aryl or heterocycle, c) halogen, d) HO, e)

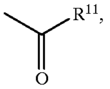

f) $—SO_2R^{11}$, or g) $N(R^{10})_2$; or $R^4$ and $R^6$ may be joined in a ring;

$R^5$ is selected from: $C_{1-4}$ alkyl, $C_{3-6}$ cycloalkyl, heterocycle, aryl, unsubstituted or substituted with:

a) $C_{1-4}$ alkoxy, b) aryl or heterocycle, c) halogen, d) HO, e)

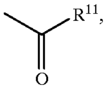

f) $—SO_2R^{11}$, or g) $N(R^{10})_2$;

$R^8$ is independently selected from:

a) hydrogen, b) aryl, heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^{10}O—$, $R^{11}S(O)_m—$, $R^{10}C(O)NR^{10}—$, $(R^{10})_2NC(O)—$, $(R10)_2N—C(NR^{10})—$, CN, $NO_2$, $R^{10}C(O)—$, $N_3$, $—N(R^{10})_2$, or $R^{11}OC(O)NR^{10}—$, and c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^{10}O—$, $R^{11}S(O)_m—$, $R^{10}C(O)NH—$, $(R^{10})_2NC(O)—$, $R^{10}{}_2N—C(NR^{10})—$, CN, $R^{10}C(O)—$, $N_3$, $—N(R^{10})_2$, or $R^{10}OC(O)NH—$;

$R^9$ is selected from:

a) hydrogen, b) alkenyl, alkynyl, perfluoroalkyl, F, Cl, Br, $R^{10}O—$, $R^{11}S(O)_m—$, $R^{10}C(O)NR^{10}—$, $(R^{10})_2NC(O)—$, $R^{10}{}_2N—C(NR^{10})—$, CN, $NO_2$, $R^{10}C(O)—$, $N_3$, $—N(R^{10})_2$, or $R^{11}OC(O)NR^{10}—$, and c) $C_1$–$C_6$ alkyl unsubstituted or substituted by perfluoroalkyl, F, Cl, Br, $R^{10}O—$, $R^1S(O)_m—$, $R^{10}C(O)NR^{10}—$, $(R^{10})_2NC(O)—$, $R^{10}{}_2N—C(NR^{10})—$, CN, $R^{10}C(O)—$, $N_3$, $—N(R^{10})_2$, or $R^{11}OC(O)NR^{10}—$;

$R^{10}$ is independently selected from hydrogen, $C_1$–$C_{14}$ alkyl, unsubstituted or substituted benzyl and unsubstituted or substituted aryl;

$R^{11}$ is independently selected from $C_1$–$C_6$ alkyl and unsubstituted or substituted aryl;

$A^1$ and $A^2$ are independently selected from: a bond, —CH═CH—, —C≡C—, —C(O)—, $—C(O)NR^{10}—$, $—NR^{10}C(O)—$, O, $—N(R^{10})—$, $—S(O)_2N(R^{10})—$, $—N(R^{10})S(O)_2—$, or $S(O)_m$;

$A^3$ is selected from:

a) a bond, b) unsubstituted or substituted aryl, and c) unsubstituted or substituted heteroaryl;

$G^1$ and $G^2$ are independently selected from: O or $H_2$;

V is selected from:

a) hydrogen, b) heterocycle, c) aryl, d) $C_1$–$C_{20}$ alkyl wherein from 0 to 4 carbon atoms are replaced with a heteroatom selected from O, S, and N, and e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

X is selected from a bond, $—CH_2—$, —C(=O)—, or $—S(=O)_m—$;

Y is selected from: a bond, —CH═CH—, —C(O)—, $—C(O)NR^{10}—$, $—NR^{10}C(O)—$, O, $—N(R^{10})—$, $—S(O)_2N(R^{10})—$, $—N(R^{10})S(O)_2—$, or $S(O)_m$;

Z is selected from:

1) an unsubstituted or substituted group selected from aryl, heteroaryl, arylmethyl, heteroarylmethyl, arylsulfonyl, and heteroarylsulfonyl, wherein the substituted group is substituted with one or more of:

a) $C_{1-4}$ alkyl, unsubstituted or substituted with: $C_{1-4}$ alkoxy, $NR^4R^6$, $C_{3-6}$ cycloalkyl, unsubstituted or substituted aryl, heterocycle, HO, $—S(O)_mR^5$, or $—C(O)NR^4R^6$, b) aryl or heterocycle, c) halogen, d) $OR^4$, e) $NR^4R^6$, f) CN, g) $NO_2$, h) $CF_3$, i) $—S(O)_mR^5$, j) $—C(O)NR^4R^6$, or k) $C_3–C_6$ cycloalkyl; or 2) an unsubstituted or substituted group selected from the group consisting of $C_1–C_6$ alkyl and $C_3–C_6$ cycloalkyl, wherein the substituted group is substituted with one or two of the following:

a) $C_{1-4}$ alkoxy, b) $NR^4R^6$, c) $C_{3-6}$ cycloalkyl d) $—NR^4C(O)R^6$, e) HO, f) $—S(O)_mR^5$, g) halogen, or h) perfluoroalkyl;

m is 0, 1 or 2;

n is 0, 1, 2, 3 or 4;

p is 0, 1, 2, 3 or 4;

q is 1 or 2;

r is 0, 1, 2, 3, 4 or5; provided that r is 0 when V is hydrogen;

t is 0 or 1; and u is 4 or 5;

or the pharmaceutically acceptable salts thereof.

In a second embodiment of this invention, the inhibitors of farnesyl-protein transferase are illustrated by the formula B:

or substituted heterocycle,

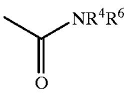 or 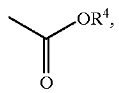

wherein the substituted group is substituted with one or more of:

1) aryl or heterocycle, unsubstituted or substituted with:

a) $C_{1-4}$ alkyl, b) $(CH_2)_pOR^4$, c) $(CH_2)_pNR^4R^6$, d) halogen, e) CN,

2) $C_{3-6}$ cycloalkyl,

3) $OR^4$,

4) $SR^5$, $S(O)R^5$, $SO_2R^5$,

5) $—NR^4R^6$,

6)

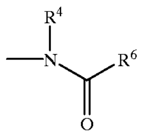

B

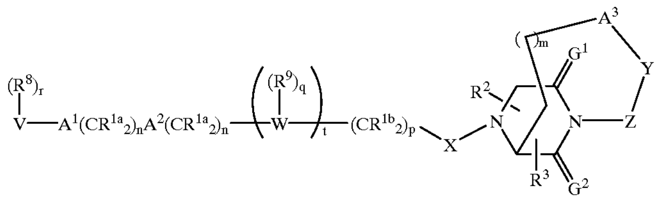

wherein:

$R^{1a}$ and $R^{1b}$ are independently selected from:

a) hydrogen, b) aryl, heterocycle, $C_3–C_{10}$ cycloalkyl, $C_2–C_6$ alkenyl, $C_2–C_6$ alkynyl, $R^{10}O—$, $R^{11}S(O)_m—$, $R^{10}C(O)NR^{10}—$, $CN(R^{10})_2NC(O)—$, $(R^{10})_2N—C(NR^{10})—$, CN, $NO_2$, $R^{10}C(O)—$, $N_3$, $—N(R^{10})_2$, or $R^{11}OC(O)NR^{10}—$, c) unsubstituted or substituted $C_1–C_6$ alkyl wherein the substitutent on the substituted $C_1–C_6$ alkyl is selected from unsubstituted or substituted aryl, heterocyclic, $C_3–C_{10}$ cycloalkyl, $C_2–C_6$ alkenyl, $C_2–C_6$ alkynyl, $R^{10}O—$, $R^{11}S(O)_m—$, $R^{10}C(O)NR^{10}—$, $(R^{10})_2NC(O)—$, CN, $(R^{10})_2N—C(NR^{10})—$, $R^{10}C(O)—$, $N_3$, $—N(R^{10})_2$, and $R^{11}OC(O)—NR^{10}—$;

$R^2$ and $R^3$ are independently selected from: H, unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted -continued

7)

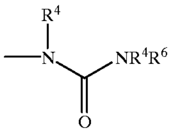

8)

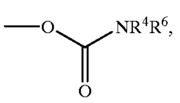

9)

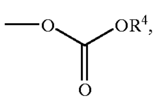

-continued

10)

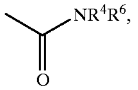

11)

$—SO_2—NR^4R^6$,

12)

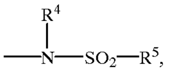

13)

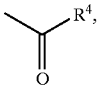

14)

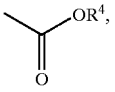

15) $N_3$, or

16) F; or $R^2$ and $R^3$ are attached to the same C atom and are combined to form $—(CH_2)_u—$ wherein one of the carbon atoms is optionally replaced by a moiety selected from: O, $S(O)_m$, —NC(O)—, and $—N(COR^{10})—$;

and $R^2$ and $R^3$ are optionally attached to the same carbon atom;

$R^4$ and $R^6$ are independently selected from: H, $C_{1-4}$ alkyl, $C_{3-6}$ cycloalkyl, heterocycle, aryl, aroyl, heteroaroyl, arylsulfonyl, heteroarylsulfonyl, unsubstituted or substituted with:

a) $C_{1-4}$ alkoxy, b) aryl or heterocycle, c) halogen, d) HO, e)

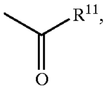

f) $—SO_2R^{11}$, or g) $N(R^{10})_2$; or $R^4$ and $R^6$ may be joined in a ring;

$R^5$ is selected from: $C_{1-4}$ alkyl, $C_{3-6}$ cycloalkyl, heterocycle, aryl, unsubstituted or substituted with:

a) $C_{1-4}$ alkoxy, b) aryl or heterocycle, c) halogen, d) HO, e)

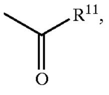

f) $—SO_2R^{11}$, or g) $N(R^{10})_2$;

$R^8$ is independently selected from:

a) hydrogen, b) aryl, heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^{10}O—$, $R^{11}S(O)_m—$, $R^{10}C(O)NR^{10}—$, $(R^{10})_2NC(O)—$, $(R^{10})_2N—C(NR^{10})—$, CN, $NO_2$, $R^{10}C(O)—$, $N_3$, $—N(R^{10})_2$, or $R^{11}OC(O)NR^{10}—$, and c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^{10}O—$, $R^{11}S(O)_m—$, $R^{10}C(O)NH—$, $(R^{10})_2NC(O)—$, $R^{10}{}_2N—C(NR^{10})—$, CN, $R^{10}C(O)—$, $N_3$, $—N(R^{10})_2$, or $R^{10}OC(O)NH—$;

$R^9$ is selected from:

a) hydrogen, b) alkenyl, alkynyl, perfluoroalkyl, F, Cl, Br, $R^{10}O—$, $R^{11}S(O)_m—$, $R^{10}C(O)NR^{10}—$, $(R^{10})_2NC(O)—$, $R^{10}{}_2N—C(NR^{10})—$, CN, $NO_2$, $R^{10}C(O)—$, $N_3$, $—N(R^{10})_2$, or $R^{11}OC(O)NR^{10}—$, and c) $C_1$–$C_6$ alkyl unsubstituted or substituted by perfluoroalkyl, F, Cl, Br, $R^{10}O—$, $R^{11}S(O)_m—$, $R^{10}C(O)NR^{10}—$, $(R^{10})_2NC(O)—$, $R^{10}{}_2N—C(NR^{10})—$, CN, $R^{10}C(O)—$, $N_3$, $—N(R^{10})_2$, or $R^{11}OC(O)NR^{10}—$;

$R^{10}$ is independently selected from hydrogen, $C_1$–$C_{14}$ alkyl, unsubstituted or substituted benzyl and unsubstituted or substituted aryl;

$R^{11}$ is independently selected from $C_1$–$C_6$ alkyl and unsubstituted or substituted aryl;

$A^1$ and $A^2$ are independently selected from: a bond, —CH═CH—, —C≡C—, —C(O)—, $—C(O)NR^{10}—$, $—NR^{10}C(O)—$, O, $—N(R^{10})—$, $—S(O)_2N(R^{10})—$, $—N(R^{10})S(O)_2—$, or $S(O)_m$;

$A^3$ is selected from:

a) a bond, b) unsubstituted or substituted aryl, or c) unsubstituted or substituted heteroaryl;

$G^1$ and $G^2$ are independently selected from: O or $H_2$;

V is selected from:

a) hydrogen, b) heterocycle, c) aryl, d) $C_1$–$C_{20}$ alkyl wherein from 0 to 4 carbon atoms are replaced with a heteroatom selected from O, S, and N, and e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

X is selected from a bond, $—CH_2—$, —C(═O)—, or $—S(═O)_m—$;

Y is selected from: a bond, —CH═CH—, —C(O)—, $—C(O)NR^{10}—$, $—NR^{10}C(O)—$, O, $—N(R^{10})—$, $—S(O)_2N(R^{10})—$, $—N(R^{10})S(O)_2—$, or $S(O)_m$;

Z is selected from:

1) an unsubstituted or substituted group selected from aryl, heteroaryl, arylmethyl, heteroarylmethyl, arylsulfonyl, heteroarylsulfonyl, wherein the substituted group is substituted with one or more of:

a) $C_{1-4}$ alkyl, unsubstituted or substituted with: $C_{1-4}$ alkoxy, $NR^4R^6$, $C_{3-6}$ cycloalkyl, unsubstituted or substituted aryl, heterocycle, HO, $—S(O)_mR^5$, or $—C(O)NR^4R^6$, b) aryl or heterocycle, c) halogen, d) $OR^4$,
e) $NR^4R^6$,
f) CN,
g) $NO_2$,
h) $CF_3$,
i) $—S(O)_mR^5$,
j) $—C(O)NR^4R^6$, or
k) $C_3$–$C_6$ cycloalkyl; or 2) an unsubstituted or substituted group selected from $C_1$–$C_6$ alkyl or $C_3$–$C_6$ cycloalkyl, wherein the substituted group is substituted with one or two of the following:
a) $C_{1-4}$ alkoxy,
b) $NR^4R^6$,
c) $C_{3-6}$ cycloalkyl
d) $—NR^4C(O)R^6$,
e) HO,
f) $—S(O)_mR^5$,
g) halogen, or
h) perfluoroalkyl;

m is 0, 1 or 2;
n is 0, 1, 2, 3 or 4;
p is 0, 1, 2, 3 or 4;
q is 1 or 2;
r is 0, 1, 2, 3, 4, or 5; provided that r is 0 when V is hydrogen;
t is 0 or 1; and
u is 4 or 5;
or the pharmaceutically acceptable salts thereof.

In another embodiment of this invention, the inhibitors of farnesyl-protein transferase are illustrated by the formula C:

C

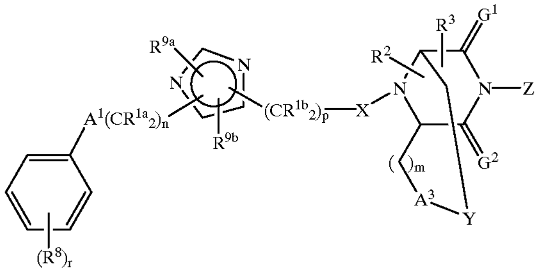

wherein:

$R^{1a}$ is selected from: hydrogen, $C_3$–$C_{10}$ cycloalkyl or $C_1$–$C_6$ alkyl;

$R^{1b}$ is independently selected from:
a) hydrogen,
b) aryl, heterocycle, $C_3$–$C_{10}$ cycloalkyl, $R^{10}O—$, $—N(R^{10})_2$, or $C_2$–$C_6$ alkenyl, and
c) $C_1$–$C_6$ alkyl unsubstituted or substituted by aryl, heterocycle, $C_3$–$C_{10}$ cycloalkyl, $C_2$–$C_6$ alkenyl, $R^{10}O—$, or $—N(R^{10})_2$;

$R^3$ is selected from H and $CH_3$;

$R^2$ is selected from: H;

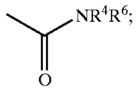

or $C_{1-5}$ alkyl, unbranched or branched, unsubstituted or substituted with one or more of:
1) aryl,
2) heterocycle,
3) $OR^4$,
4) $SR^5$, $SO_2R^5$, or
5)

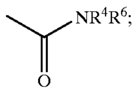

and $R^2$ and $R^3$ are optionally attached to the same carbon atom;

$R^4$ and $R^6$ are independently selected from:
H, $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;

$R^5$ is selected from:
$C_{1-4}$ alkyl or $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O—$, $R^{10}C(O)NR^{10}—$, CN, $NO_2$, $(R^{10})_2N—C(NR^{10})—$, $R^{10}C(O)—$, $R^{10}OC(O)—$, $—N(R^{10})_2$, or $R^{11}OC(O)NR^{10}—$, and
c) $C_1$–$C_6$ alkyl substituted by $C_1$–$C_6$ perfluoroalkyl, $R^{10}O—$, $R^{10}C(O)NR^{10}—$, $(R^{10})_2N—C(NR^{10})—$, $R^{10}C(O)—$, $R^{10}OC(O)—$, $—N(R^{10})_2$, or $R^{11}OC(O)NR^{10}—$;

$R^{9a}$ and $R^{9b}$ are independently selected from hydrogen, ethyl, cyclopropyl or methyl;

$R^{10}$ is independently selected from hydrogen, $C_1$–$C_{14}$ alkyl, substituted or unsubstituted benzyl and substituted or unsubstituted aryl;

$R^{11}$ is independently selected from $C_1$–$C_6$ alkyl and substituted or unsubstituted aryl;

$A^1$ is selected from: a bond, —C(O)—, O, $—N(R^{10})—$, or $S(O)_m$;

$A^3$ is selected from:
a) a bond,
b) unsubstituted or substituted aryl, and
c) unsubstituted or substituted heteroaryl;

$G^1$ and $G^2$ are independently selected from: O or $H_2$;

X is selected from a bond, $—CH_2—$, —C(=O)—, or $—S(=O)_m—$;

Y is selected from: a bond O;

Z is an unsubstituted or substituted aryl, wherein the substituted aryl is substituted with one or more of the following:
a) $C_{1-4}$ alkyl, unsubstituted or substituted with:
1) $C_{1-4}$ alkoxy,
2) $NR^4R^6$,
3) $C_{3-6}$ cycloalkyl,
4) unsubstituted or substituted aryl,
5) heterocycle,
6) HO,
7) $—S(O)_mR^5$, or
8) $—C(O)NR^4R^6$,
b) aryl or heterocycle, c) halogen, d) $OR^4$, e) $NR^4R^6$, f) CN, g) $NO_2$, h) $CF_3$, i) $—S(O)_mR^5$, j) $—C(O)NR^4R^6$, or k) $C_3$–$C_6$ cycloalkyl;

m is 0, 1 or 2;

n is 0 or 1; provided that n is not 0 if $A^1$ is a bond, O, $—N(R^{10})—$ or $S(O)_m$;

p is 0, 1, 2, 3 or 4; and r is 0, 1, 2, 3, 4, or 5;

or the pharmaceutically acceptable salts thereof.

In a further embodiment of this invention, the inhibitors of farnesyl-protein transferase are illustrated by the formula D:

D

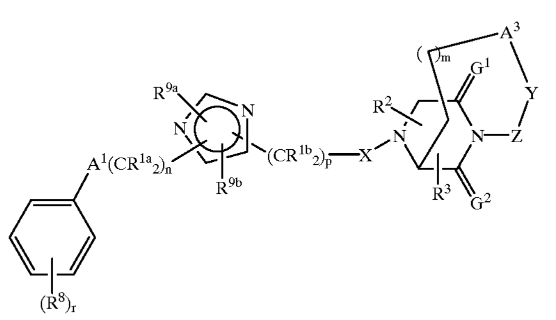

wherein:

$R^{1a}$ is selected from: hydrogen, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^{10}O—$, $—N(R^{10})_2$, or $C_2$–$C_6$ alkenyl, and c) $C_1$–$C_6$ alkyl unsubstituted or substituted by aryl, heterocycle, $C_3$–$C_{10}$ cycloalkyl, $C_2$–$C_6$ alkenyl, $R^{10}O—$, or $—N(R^{10})_2$;

$R^3$ is selected from H and $CH_3$;

$R^2$ is selected from: H;

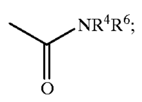

or $C_{1-5}$ alkyl, unbranched or branched, unsubstituted or substituted with one or more of:

1) aryl, 2) heterocycle,

3) $OR^4$,

4) $SR^5$, $SO_2R^5$, or

5)

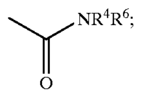

and $R^2$ and $R^3$ are optionally attached to the same carbon atom;

$R^4$ and $R^6$ are independently selected from:

H, $C_{1-4}$ alkyl, $C_{3-6}$ cycloalkyl, aryl, heterocycle, unsubstituted or substituted with:

a) $C_{1-4}$ alkoxy, b) halogen, or c) aryl or heterocycle;

$R^5$ is selected from:

$C_{1-4}$ alkyl or $C_{3-6}$ cycloalkyl, unsubstituted or substituted with:

a) $C_{1-4}$ alkoxy, b) halogen, or c) aryl or heterocycle;

$R^8$ is independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O—$, $R^{10}C(O)NR^{10}—$, CN, $NO_2$, $(R^{10})_2N—C(NR^{10})—$, $R^{10}C(O)—$, $R^{10}OC(O)—$, $—N(R^{10})_2$, or $R^{11}OC(O)NR^{10}—$, and c) $C_1$–$C_6$ alkyl substituted by $C_1$–$C_6$ perfluoroalkyl, $R^{10}O—$, $R^{10}C(O)NR^{10}—$, $(R^{10})_2N—C(NR^{10})—$, $R^{10}C(O)—$, $R^{10}OC(O)—$, $—N(R^{10})_2$, or $R^{11}OC(O)NR^{10}—$;

$R^{9a}$ and $R^{9b}$ are independently selected from hydrogen, ethyl, cyclopropyl or methyl;

$R^{10}$ is independently selected from hydrogen, $C_1$–$C_{14}$ alkyl, substituted or unsubstituted benzyl and substituted or unsubstituted aryl;

$R^{11}$ is independently selected from $C_1$–$C_6$ alkyl and substituted or unsubstituted aryl;

$A^1$ is selected from: a bond, $—C(O)—$, O, $—N(R^{10})—$, or $S(O)_m$;

$A^3$ is selected from:

a) a bond, b) unsubstituted or substituted aryl, and c) unsubstituted or substituted heteroaryl;

$G^1$ and $G^2$ are independently selected from: O or $H_2$;

X is selected from a bond, $—CH_2—$, $—C(=O)—$, or $—S(=O)_m$;

Y is selected from: a bond O;

Z is an unsubstituted or substituted aryl, wherein the substituted aryl is substituted with one or more of the following:

a) $C_{1-4}$ alkyl, unsubstituted or substituted with:

1) $C_{1-4}$ alkoxy,

2) $NR^4R^6$,

3) $C_{3-6}$ cycloalkyl, 4) unsubstituted or substituted aryl, 5) heterocycle,

6) HO,

7) $—S(O)_mR^5$, or

8) $—C(O)NR^4R^6$, b) aryl or heterocycle, c) halogen, d) $OR^4$, e) $NR^4R^6$, f) CN, g) $NO_2$,
h) $CF_3$,
i) $—S(O)_mR^5$,
j) $—C(O)NR^4R^6$, or
k) $C_3–C_6$ cycloalkyl;

m is 0, 1 or 2;

n is 0 or 1; provided that n is not 0 if $A^1$ is a bond, O, $—N(R^{10})—$ or $S(O)_m$;

p is 0, 1, 2, 3 or 4; and r is 0, 1, 2, 3, 4 or 5;

or the pharmaceutically acceptable salts thereof.

In a further embodiment of this invention, the inhibitors of farnesyl-protein transferase are illustrated by the formula E:

E

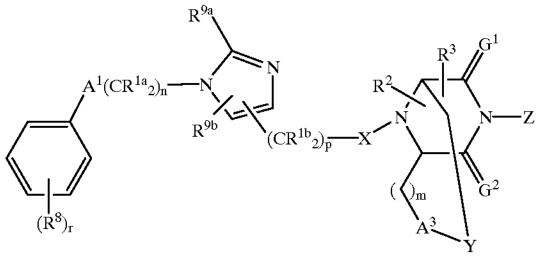

wherein:

$R^{1a}$ is selected from: hydrogen, $C_3–C_{10}$ cycloalkyl or $C_1–C_6$ alkyl;

$R^{1b}$ is independently selected from:
a) hydrogen,
b) aryl, heterocycle, $C_3–C_{10}$ cycloalkyl, $R^{10}O—$, $—N(R^{10})_2$, or $C_2–C_6$ alkenyl, and
c) $C_1–C_6$ alkyl unsubstituted or substituted by aryl, heterocycle, $C_3–C_{10}$ cycloalkyl, $C_2–C_6$ alkenyl, $R^{10}O—$, or $—N(R^{10})_2$;

$R^3$ is selected from H and $CH_3$;

$R^2$ is selected from: H;

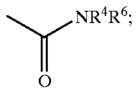

or $C_{1-5}$ alkyl, unbranched or branched, unsubstituted or substituted with one or more of:
1) aryl,
2) heterocycle,
3) $OR^4$,
4) $SR^5$, $SO_2R^5$, or
5)

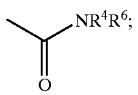

and $R^2$ and $R^3$ are optionally attached to the same carbon atom;

$R^4$ and $R^6$ are independently selected from:
H, $C_{1-4}$ alkyl, $C_{3-6}$ cycloalkyl, aryl, heterocycle, unsubstituted or substituted with:
a) $C_{1-4}$ alkoxy,
b) halogen, or
c) aryl or heterocycle;

$R^5$ is selected from:
$C_{1-4}$ alkyl or $C_{3-6}$ cycloalkyl, unsubstituted or substituted with:
a) $C_{1-4}$ alkoxy,
b) halogen, or
c) aryl or heterocycle;

$R^8$ is independently selected from:
a) hydrogen,
b) $C_1–C_6$ alkyl, $C_2–C_6$ alkenyl, $C_2–C_6$ alkynyl, $C_1–C_6$ perfluoroalkyl, F, Cl, $R^{10}O—$, $R^{10}C(O)NR^{10}—$, CN, $NO_2$, $(R^{10})_2N—C(NR^{10})—$, $R^{10}C(O)—$, $R^{10}OC(O)—$, $—N(R^{10})_2$, or $R^{11}OC(O)NR^{10}—$, and
c) $C_1–C_6$ alkyl substituted by $C_1–C_6$ perfluoroalkyl, $R^{10}O—$, $R^{10}C(O)NR^{10}—$, $(R^{10})_2N—C(NR^{10})—$, $R^{10}OC(O)—$, $R^{10}OC(O)—$, $—N(R^{10})_2$, or $R^{11}OC(O)NR^{10}—$;

$R^{9a}$ and $R^{9b}$ are independently selected from hydrogen, ethyl, cyclopropyl or methyl;

$R^{10}$ is independently selected from hydrogen, $C_1–C_{14}$ alkyl, substituted or unsubstituted benzyl and substituted or unsubstituted aryl;

$R^{11}$ is independently selected from $C_1–C_6$ alkyl and substituted or unsubstituted aryl;

$A^1$ is selected from: a bond, —C(O)—, O, $—N(R^{10})—$, or $S(O)_m$;

$A^3$ is selected from:
a) a bond,
b) unsubstituted or substituted aryl, and
c) unsubstituted or substituted heteroaryl;

X is selected from a bond, $—CH_2—$, —C(=O)—, or $—S(=O)_m$;

$G^1$ and $G^2$ are independently selected from: O or $H_2$;

Y is selected from: a bond O;

Z is an unsubstituted or substituted aryl, wherein the substituted aryl is substituted with one or more of the following:
a) $C_{1-4}$ alkyl, unsubstituted or substituted with:
1) $C_{1-4}$ alkoxy,
2) $NR^4R^6$,
3) $C_{3-6}$ cycloalkyl,
4) unsubstituted or substituted aryl,
5) heterocycle,
6) HO,
7) $—S(O)_mR^5$, or
8) $—C(O)NR^4R^6$,
b) aryl or heterocycle,
c) halogen,
d) $OR^4$,
e) $NR^4R^6$,
f) CN,
g) $NO_2$,
h) $CF_3$,
i) $—S(O)_mR^5$,
j) $—C(O)NR^4R^6$, or
k) $C_3–C_6$ cycloalkyl;

m is 0, 1 or 2;

n is 0 or 1; provided that n is not 0 if $A^1$ is a bond, O, $—N(R^{10})—$ or $S(O)_m$;

p is 0, 1, 2, 3 or 4; and r is 0, 1, 2, 3, 4, or 5;

or the pharmaceutically acceptable salts thereof.

In a further embodiment of this invention, the inhibitors of farnesyl-protein transferase are illustrated by the formula

F:

F

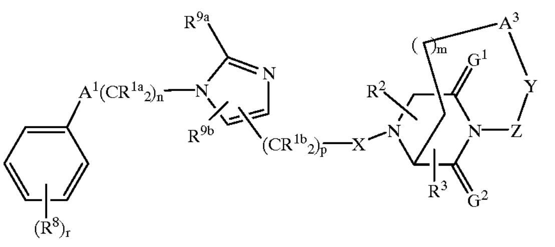

wherein:

$R^{1a}$ is selected from: hydrogen, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^{10}O$—, —$N(R^{10})_2$, or $C_2$–$C_6$ alkenyl, and c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^3$ is selected from H and $CH_3$;

$R^2$ is selected from: H;

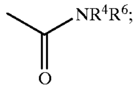

or $C_{1-5}$ alkyl, unbranched or branched, unsubstituted or substituted with one or more of:

1) aryl, 2) heterocycle,

3) $OR^4$,

4) $SR^5$, $SO_2R^5$, or

5)

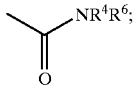

and $R^2$ and $R^3$ are optionally attached to the same carbon atom;

$R^4$ and $R^6$ are independently selected from:

H, $C_{1-4}$ alkyl, $C_{3-6}$ cycloalkyl, aryl, heterocycle, unsubstituted or substituted with:

a) $C_{1-4}$ alkoxy, b) halogen, or c) aryl or heterocycle;

$R^5$ is selected from:

$C_{1-4}$ alkyl or $C_{3-6}$ cycloalkyl, unsubstituted or substituted with:

a) $C_{1-4}$ alkoxy, b) halogen, or c) aryl or heterocycle;

$R^8$ is independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{9a}$ and $R^{9b}$ are independently selected from hydrogen, ethyl, cyclopropyl or methyl;

$R^{10}$ is independently selected from hydrogen, $C_1$–$C_{14}$ alkyl, substituted or unsubstituted benzyl and substituted or unsubstituted aryl;

$R^{11}$ is independently selected from $C_1$–$C_6$ alkyl and substituted or unsubstituted aryl;

$A^1$ is selected from: a bond, —C(O)—, O, —$N(R^{10})$—, or $S(O)_m$;

$A^3$ is selected from:

a) a bond, b) unsubstituted or substituted aryl, and c) unsubstituted or substituted heteroaryl;

$G^1$ and $G^2$ are independently selected from: O or $H_2$;

X is selected from a bond, —$CH_2$—, —C(=O)—, or —$S(=O)_m$—;

Y is selected from: a bond O;

Z is an unsubstituted or substituted aryl, wherein the substituted aryl is substituted with one or more of the following:

a) $C_{1-4}$ alkyl, unsubstituted or substituted with:

1) $C_{1-4}$ alkoxy,

2) $NR^4R^6$,

3) $C_{3-6}$ cycloalkyl, 4) unsubstituted or substituted aryl, 5) heterocycle,

6) HO,

7) —$S(O)_mR^5$, or

8) —$C(O)NR^4R^6$, b) aryl or heterocycle, c) halogen, d) $OR^4$, e) $NR^4R^6$, f) CN, g) $NO_2$, h) $CF_3$, i) —$S(O)_mR^5$, j) —$C(O)NR^4R^6$, or k) $C_3$–$C_6$ cycloalkyl;

m is 0, 1 or 2;

n is 0 or 1; provided that n is not 0 if $A^1$ is a bond, O, —$N(R^{10})$— or $S(O)_m$;

p is 0, 1, 2, 3 or 4; and r is 0, 1, 2, 3, 4 or 5;

or the pharmaceutically acceptable salts thereof.

The specific compounds of this invention are as follows:

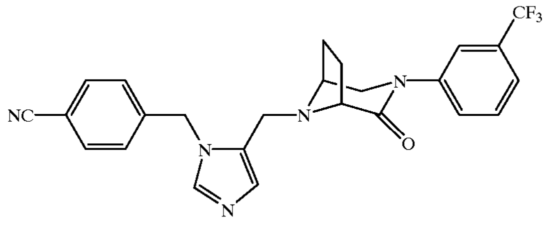

1(R),5(S)-3-[(3-trifluoromethyl)phenyl]-8-[(4-cyanobenzyl)-5-imidazolylmethyl]-3,8-diaza-2-oxobicyclo[3.2.1]octane;

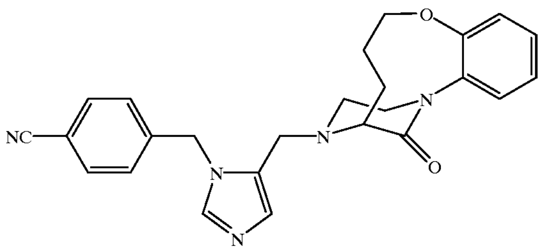

(±)-9-[1-(4-cyanobenzyl)-5-imidazolylmethyl]-b-benzo-1,9-diaza-4-oxa-12-oxobicyclo[6.3.1]dodecane;

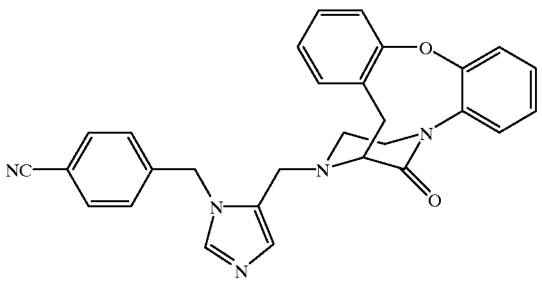

(±)-9-[1-(4-cyanobenzyl)-5-imidazolylmethyl]-1,9-diaza-b,e-dibenzo-4-oxa-12-oxobicyclo[6.3.1]dodecane; and

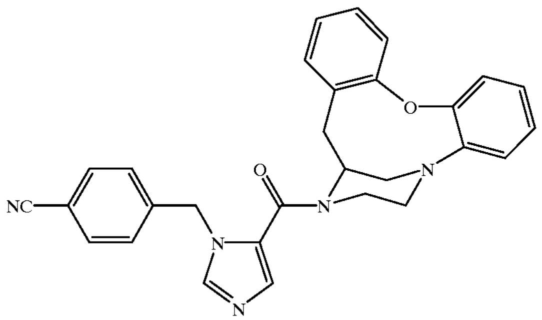

(±)-9-[1-(4-cyanobenzyl)-5-imidazolylcarbonyl]-1,9-diaza-b,e-dibenzo-4-oxa-bicyclo[6.3.1]dodecane or the optical isomers or the pharmaceutically acceptable salts thereof.

The compounds of the present invention may have asymmetric centers and occur as racemates, racemic mixtures, and as individual diastereomers, with all possible isomers, including optical isomers, being included in the present invention. When any variable (e.g. aryl, heterocycle, $R^1$, $R^2$ etc.) occurs more than one time in any constituent, its definition on each occurence is independent at every other occurence. Also, combinations of substituents/or variables are permissible only if such combinations result in stable compounds.

As used herein, "alkyl" is intended to include both branched and straight-chain saturated aliphatic hydrocarbon groups having the specified number of carbon atoms; "alkoxy" represents an alkyl group of indicated number of carbon atoms attached through an oxygen bridge. "Halogen" or "halo" as used herein means fluoro, chloro, bromo and iodo.

As used herein, "aryl" is intended to mean any stable monocyclic or bicyclic carbon ring of up to 7 members in each ring, wherein at least one ring is aromatic. Examples of such aryl elements include phenyl, naphthyl, tetrahydronaphthyl, indanyl, biphenyl, phenanthryl, anthryl or acenaphthyl.

As used herein, "aroyl" is intended to mean any stable monocyclic or bicyclic carbon ring of up to 7 members in each ring, wherein at least one ring is aromatic and at least one ring is attached to a carboxy. Examples of such aroyl elements include benzoyl and naphthoyl.

The term heterocycle or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl.

As used herein, "heteroaryl" is intended to mean any stable monocyclic or bicyclic carbon ring of up to 7 members in each ring, wherein at least one ring is aromatic and wherein from one to four carbon atoms are replaced by heteroatoms selected from the group consisting of N, O, and S. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrimidinyl, pyrrolyl, quinazolinyl, quinolinyl, quinoxalinyl, tetrahydroisoquinolinyl, tetrahydroquinolinyl, thiazolyl, thienofuryl, thienothienyl, and thienyl.

As used herein, "heteroaroyl" is intended to mean any stable monocylic or bicyclic carbon ring of up to 7 members in each ring, wherein at least one ring is aromatic and at least one ring is attached to a carboxy, and wherein from one to four carbon atoms are replaced by heteroatoms selected from the group consisting of N, O and S. Examples of such heteroaroyl elements include furoyl, thienoyl, pyrroloyl and nicotinoyl.

As used herein in the definition of $R^2$ and $R^3$, the term "the substituted group" is intended to mean a substituted $C_{1-8}$ alkyl, substituted $C_{2-8}$ alkenyl, substituted $C_{2-8}$ alkynyl, substituted aryl or substituted heterocycle from which the substitutent(s) $R^2$ and $R^3$ are selected.

As used herein, the terms "substituted aryl", "substituted heteroaryl", "substituted heterocycle", and "substituted cycloalkyl" are intended to include the cyclic group which is substituted with 1 or 2 substituents selected from the group which includes but is not limited to F, Cl, Br, $CF_3$, $NH_2$, $N(C_1$–$C_6$ alkyl$)_2$, $NO_2$, CN, $(C_1$–$C_6$ alkyl)O—, —OH, $(C_1$–$C_6$ alkyl)$S(O)_m$—, $(C_1$–$C_6$ alkyl)C(O)NH—, $H_2N$—C (NH)—, $(C_1$–$C_6$ alkyl)C(O)—, $(C_1$–$C_6$ alkyl)OC(O)—, $N_3$, $(C_1$–$C_6$ alkyl)OC(O)NH— and $C_1$–$C_{20}$ alkyl.

As used herein in the definition of $R^4$ and $R^6$ the substituted $C_{1-4}$ alkyl, substituted $C_{3-6}$ cycloalkyl, substituted aroyl, substituted aryl, substituted heteroaroyl, substituted arylsulfonyl, substituted heteroarylsulfonyl and substituted heterocycle include moieties containing from 1 to 3 substitutents in addition to the point of attachment to the rest of the compound.

When $R^2$ and $R^3$ are combined to form $—(CH_2)_u—$, cyclic moieties are formed. Examples of such cyclic moieties include, but are not limited to:

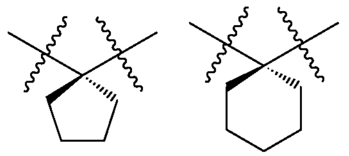

In addition, such cyclic moieties may optionally include a heteroatom(s). Examples of such heteroatom-containing cyclic moieties include, but are not limited to:

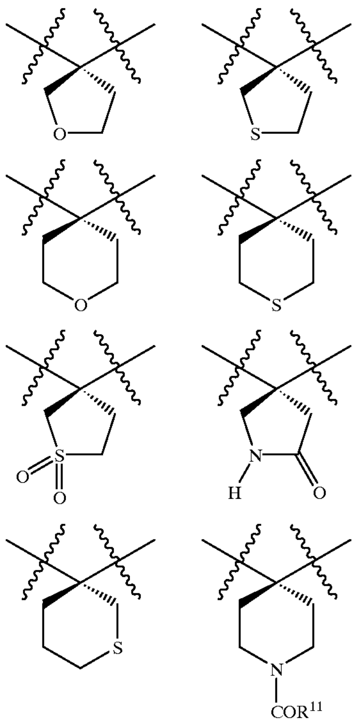

When $R^4$ and $R^6$ are combined to form a ring, cyclic amine and amide moieties are formed. Examples of such cyclic moieties include, but are not limited to:

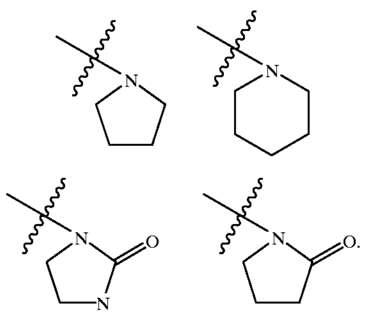

In addition, such cyclic moieties may optionally include another heteroatom(s). Examples of such heteroatom-containing cyclic amine moieties include, but are not limited to:

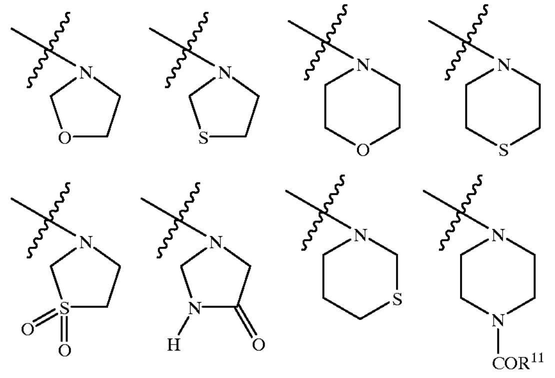

Lines drawn into the ring systems from substituents (such as from $R^2$, $R^3$, $R^4$ etc.) indicate that the indicated bond may be attached to any of the substitutable ring carbon atoms.

Preferably, $R^{1a}$ and $R^{1b}$ are independently selected from: hydrogen, $—N(R^{10})_2$, $R^{10}C(O)NR^{10}$— or unsubstituted or substituted $C_1$–$C_6$ alkyl wherein the substituent on the substituted $C_1$–$C_6$ alkyl is selected from unsubstituted or substituted phenyl, $—N(R^{10})_2$, $R^{10}O$— and $R^{10}C(O)NR^{10}$—.

Preferably, $R^2$ is selected from: H;

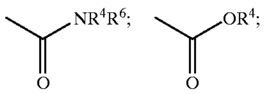

and $C_{1-5}$ alkyl, unbranched or branched, unsubstituted or substituted wherein the substituted group is substituted with one or more of:

1) aryl or heterocycle, unsubstituted or substituted with:
   a) $C_{1-4}$ alkyl,
   b) $(CH_2)_pOR^4$,
   c) $(CH_2)_pNR^4R^6$,
   d) halogen,
2) $C_{3-6}$ cycloalkyl,
3) $OR^4$,
4) $SR^5$, $S(O)R^5$, $SO_2R^5$,

5) —$NR^4R^6$,

6)

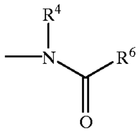

7)

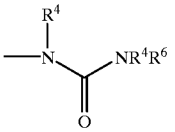

8)

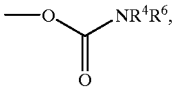

9)

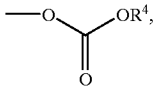

10)

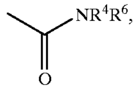

11)

—$SO_2$—$NR^4R^6$,

12)

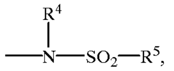

13)

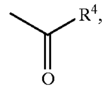

14)

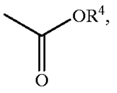

15) $N_3$, or

16) F.

Preferably, $R^3$ is selected from: hydrogen and $C_1$–$C_6$ alkyl.

Preferably, $R^4$ and $R^6$ is selected from: hydrogen, unsubstituted or substituted $C_1$–$C_6$ alkyl, unsubstituted or substituted aryl and unsubstituted or substituted cycloalkyl.

Preferably, $R^5$ is unsubstituted or substituted $C_1$–$C_6$ alkyl, unsubstituted or substituted aryl and unsubstituted or substituted cycloalkyl.

Preferably, $R^9$ is hydrogen, chloro or methyl. Most preferably, $R^9$ is hydrogen.

Preferably, $R^{10}$ is selected from H, $C_1$–$C_6$ alkyl and benzyl.

Preferably, $A^1$ and $A^2$ are independently selected from: a bond, —$C(O)NR^{10}$—, —$NR^{10}C(O)$—, O, —$N(R^{10})$—, —$S(O)_2N(R^{10})$— and —$N(R^{10})S(O)_2$—.

Preferably, $A^3$ is selected from a bond, unsubstituted or substituted aryl and unsubstituted or substituted heteroaryl.

Preferably, at least one of $G^1$ or $G^2$ is oxygen.

Preferably, W is selected from imidazolinyl, imidazolyl, oxazolyl, pyrazolyl, pyyrolidinyl, thiazolyl and pyridyl. More preferably, W is selected from imidazolyl and pyridyl.

Preferably, X is a bond, $CH_2$ or CO.

Preferably, V is selected from hydrogen, heterocycle and aryl. More preferably, V is phenyl.

Preferably, Z is selected from unsubstituted or substituted phenyl, unsubstituted or substituted naphthyl, unsubstituted or substituted pyridyl, unsubstituted or substituted furanyl and unsubstituted or substituted thienyl. More preferably, Z is unsubstituted or substituted phenyl.

Preferably, n and r are independently 0, 1, or 2.

Preferably, p is 1, 2 or 3.

Preferably, t is 1.

Preferably, the moiety

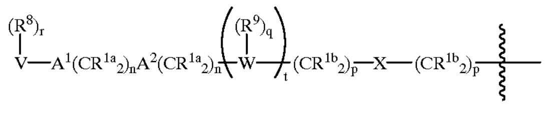

is selected from:

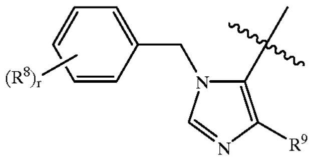

and

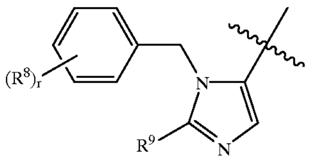

It is intended that the definition of any substituent or variable (e.g., $R^{1a}$, $R^9$, n, etc.) at a particular location in a molecule be independent of its definitions elsewhere in that molecule. Thus, —$N(R^{10})_2$ represents —NHH, —$NHCH_3$, —$NHC_2H_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like: and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like.

The pharmaceutically acceptable salts of the compounds of this invention can be synthesized from the compounds of this invention which contain a basic moiety by conventional chemical methods. Generally, the salts are prepared either by ion exchange chromatography or by reacting the free base with stoichiometric amounts or with an excess of the desired salt-forming inorganic or organic acid in a suitable solvent or various combinations of solvents.

Reactions used to generate the compounds of this invention are prepared by employing reactions as shown in the Schemes 1–15, in addition to other standard manipulations such as ester hydrolysis, cleavage of protecting groups, etc., as may be known in the literature or exemplified in the experimental procedures.

These reactions may be employed in a linear sequence to provide the compounds of the invention or they may be used to synthesize fragments which are subsequently joined by the alkylation reactions described in the Schemes.

Synopsis of Schemes 1–15:

The requisite intermediates are in some cases commercially available, or can be prepared according to literature procedures, for the most part. Final compounds can be generally prepared by reductive coupling or acylation of the requisite nitrogen-containing heterocycle with an aldehyde or carboxylic acid, respectively.

Scheme 1 illustrates the synthesis of an imidazole carboxaldehyde by selective N-alkylation chemistry. 4-hydroxymethylimidazole can be converted to the acetate I by standard procedures, and can be reacted with an alkyl halide, then treated with refluxing methanol to provide the regiospecifically alkylated imidazole II. The ester is hydrolyzed and the resulting alcohol oxidized to provide the aldehyde III.

Scheme 2 illustrates the synthesis of a representative bicyclic nitrogen-containing heterocycle synthon from a functionalized piperazinone, and its coupling with an aldehyde to give a final product. Homoserine lactone is used to prepare a Boc-protected diamine IV via protection, diisobutylaluminum hydride reduction, and reductive amination with an amine. Intermediate IV may then be acylated with chloroacetyl chloride and cyclized with base to provide piperazinone V. The hydroxyl moiety of V may be converted to a methanesulfonate leaving group, then cyclized with lithium hexamethyldisilazide, to provide the protected bicyclic amine VI. Acid-promoted deprotection to provide VII may be followed by reductive coupling with a variety of aldehydes such as III to give compound VIII. The reductive alkylation can be accomplished at a pH of about 4 to about 7 with a variety of reducing agents, such as sodium triacetoxyborohydride or sodium cyanoborohydride in a solvent such as dichloroethane, methanol or dimethylformamide. The final product XI is isolated in the salt form, for example, as a trifluoroacetate, hydrochloride or acetate salt, among others.

Scheme 3 illustrates the synthesis of an alternative variation of bicyclic nitrogen-containing heterocycle, and its coupling with an aldehyde to give a final product. A protected amine such as IX may be aminoethylated at the nitrogen by either heating with an oxazolidinone followed by N-protection, or by reductive amination of an amino aldehyde to provide X. The amino aldehydes can be prepared by standard procedures, such as that described by O. P. Goel et al. (*Organic Syntheses*, 1988, 67, 69–75), from the appropriate amino acids. The protected diamine X may be acylated with chloroacetyl chloride and cyclized with base to provide piperazinone XI. Deprotection of the ether group to give XII is followed by arylation and reduction to give an alcohol XIII. The hydroxyl moiety of XIII may be converted to a methanesulfonate leaving group, then cyclized with lithium hexamethyldisilazide, to provide the protected bicyclic amine XIV. Acid-promoted deprotection to provide XV may be followed by reductive coupling with an aldehyde such as III to give compound XVI.

Scheme 4 illustrates the synthesis of a similar bicyclic nitrogen-containing heterocycle, and its coupling with an aldehyde to give a final product. Alkylation of XVII with 1-chloro-3-iodopropane is followed by the Finkelstein reaction to give XVIII. Cyclization gives the alkyl-bridged compound XIX, and deprotection followed by reductive coupling with an aldehyde yields compound XXI.

Scheme 5 shows the oxidation of an aldehyde of interest (e.g. III) to the corresponding carboxylic acid (e.g. XXII), which may be coupled to an amine using well known amide-forming reactions. Thus, piperazine XXIV (Scheme 6), prepared by lithium aluminum hydride reduction of piperazinone intermediate XXIII, may be coupled to carboxylate XXII to provide the amide XXV.

If an amine intermediate such as XX is reductively coupled to a protected diamino aldehyde such as XXVI (Scheme 7), final product XXVIII can be prepared by deprotection of the amino groups. The diamine product XXVIII can further be selectively protected to obtain XXIX, which can subsequently be reductively alkylated with a second aldehyde to obtain XXX. Removal of the protecting group and conversion to cyclized products such as the dihydroimidazole XXXII can be accomplished by literature procedures.

If the intermediate XX is reductively alkylated with an aldehyde, which also has a protected hydroxyl group, such as XXXIII in Scheme 8, the protecting group can be subsequently removed to unmask the alcohol XXXV. The alcohol can be oxidized under standard conditions (e.g. an aldehyde), which can then be reacted with a variety of organometallic reagents such as Grignard reagents, to obtain secondary alcohols such as XXXVII. In addition, the fully deprotected amino alcohol XXXVIII (Scheme 9) can be reductively alkylated (under conditions described previously) with a variety of aldehydes to obtain secondary amines, such as IXL, or tertiary amines.

The Boc protected amino alcohol XXXV can also be utilized to synthesize 2-aziridinylmethylamines such as XL (Scheme 10). Treating XXXV with 1,1'-sulfonyldiimidazole and sodium hydride in a solvent such as dimethylformamide leads to the formation of aziridine XL. The aziridine reacts in the presence of a nucleophile, such as a thiol, in the presence of base to yield, after deprotection, the ring-opened sulfide product XLI.

In addition, the intermediate XX can be reacted with aldehydes derived from amino acids such as O-alkylated tyrosines, according to standard procedures, to obtain compounds such as XLIV as shown in Scheme 11. When R' is an aryl group, XLIV can first be hydrogenated to unmask the phenol, and the amine group deprotected with acid to produce XLV. Alternatively, the amine protecting group in XLIV can be removed, and O-alkylated phenolic amines such as XLVI produced.

Schemes 12–15 illustrate syntheses of suitably substituted aldehydes useful in the syntheses of the instant compounds wherein the variable W is present as a pyridyl moiety. Similar synthetic strategies for preparing alkanols that incorporate other heterocyclic moieties for variable W are also well known in the art.

SCHEME 1

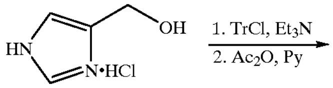

-continued
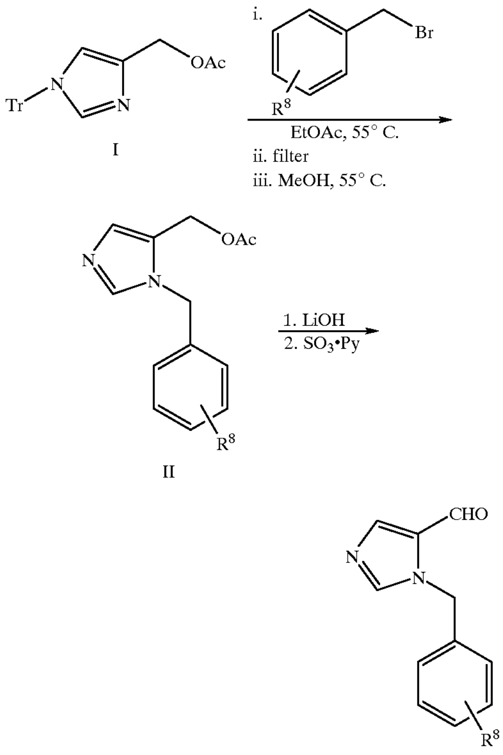
I II III
SCHEME 2
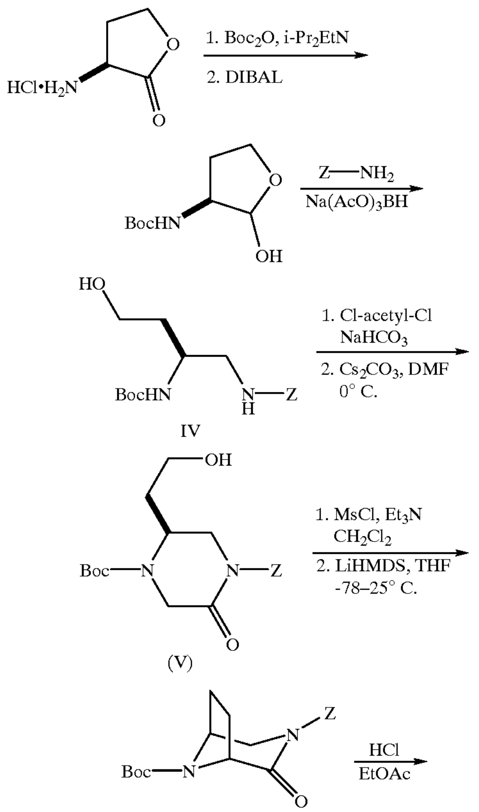
IV (V) VI
-continued
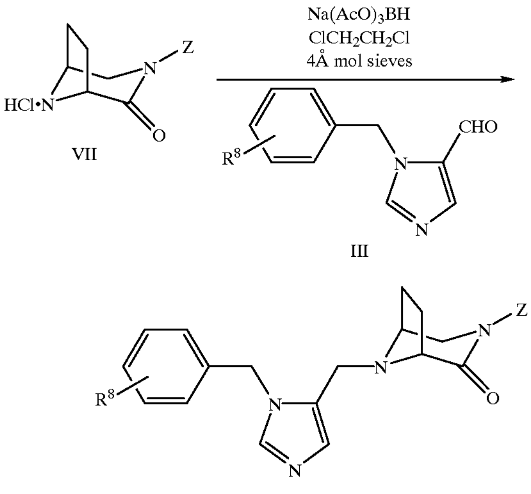
VII III VIII
SCHEME 3
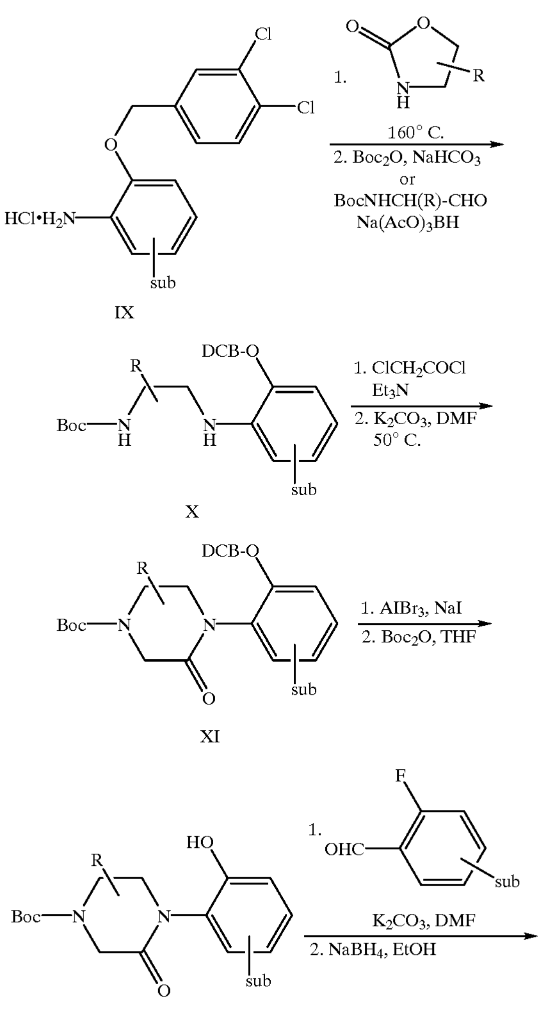
IX X XI XII 29
-continued
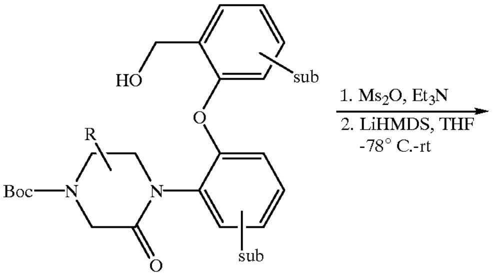
XIII
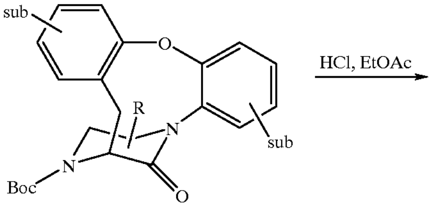
XIV
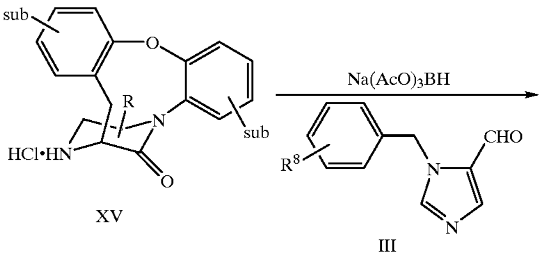
XV
III
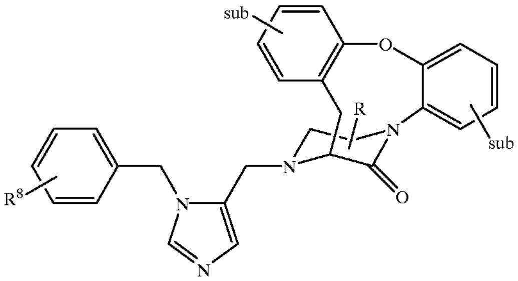
XVI
SCHEME 4
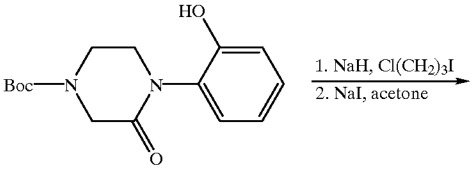
XVII
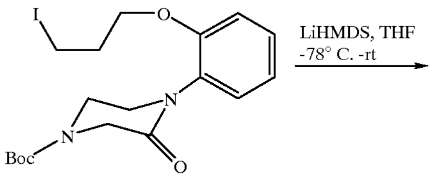
XVIII
30
-continued
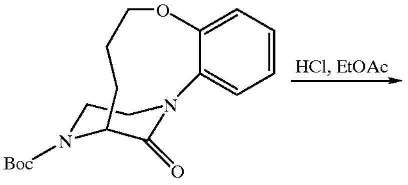
XIX
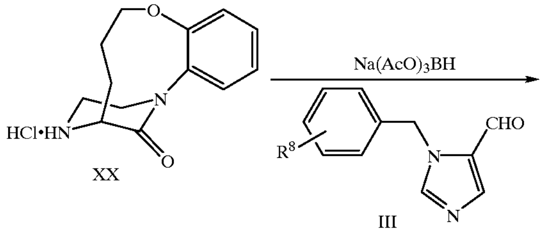
XX
III
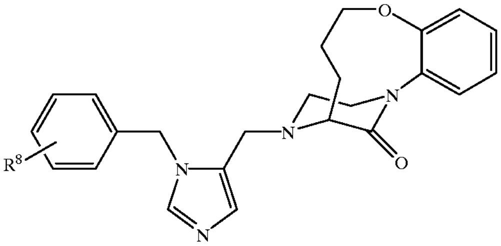
XXI
SCHEME 5
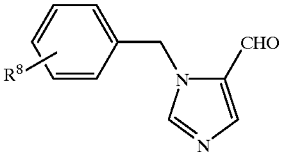
III
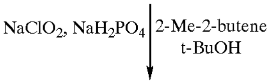
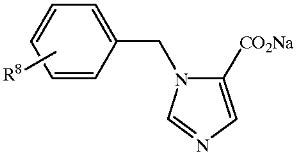
XXII SCHEME 6
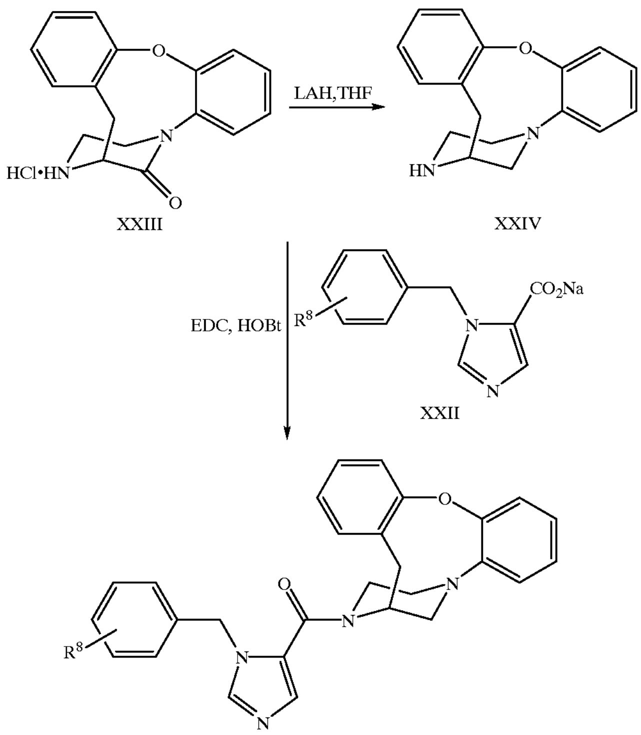
XXIII XXIV XXII XXV
SCHEME 7
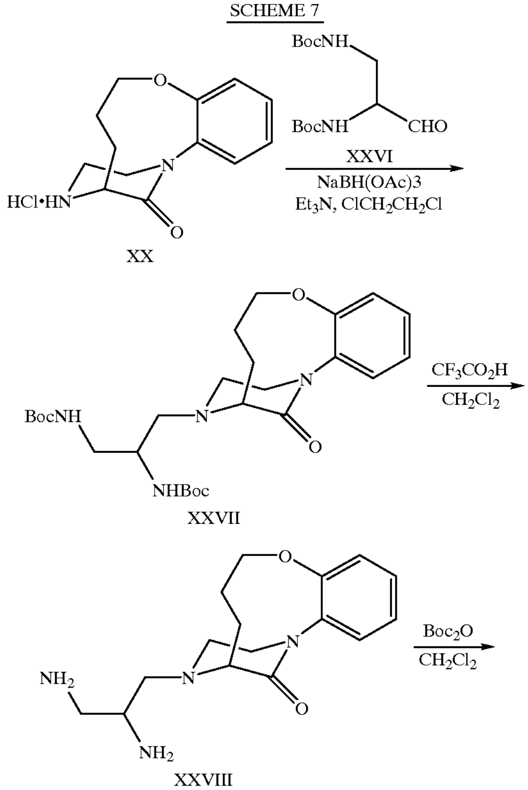
XX XXVII XXVIII
-continued
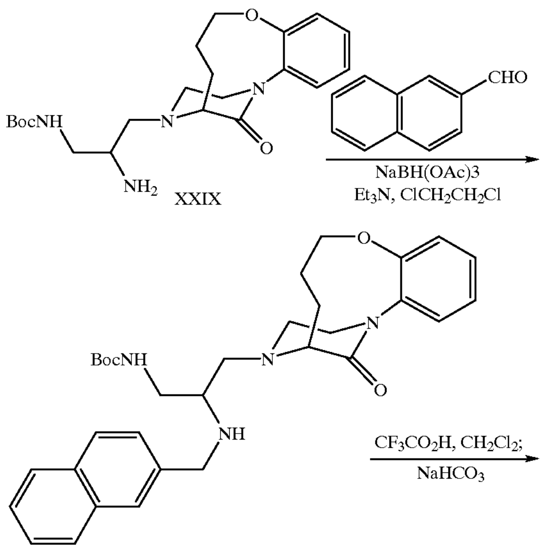
XXIX XXX -continued
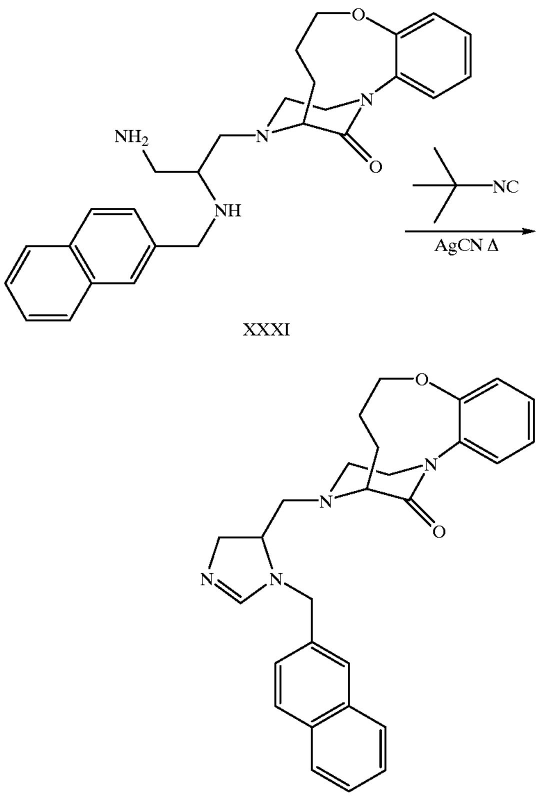
XXXI
XXXII
SCHEME 8
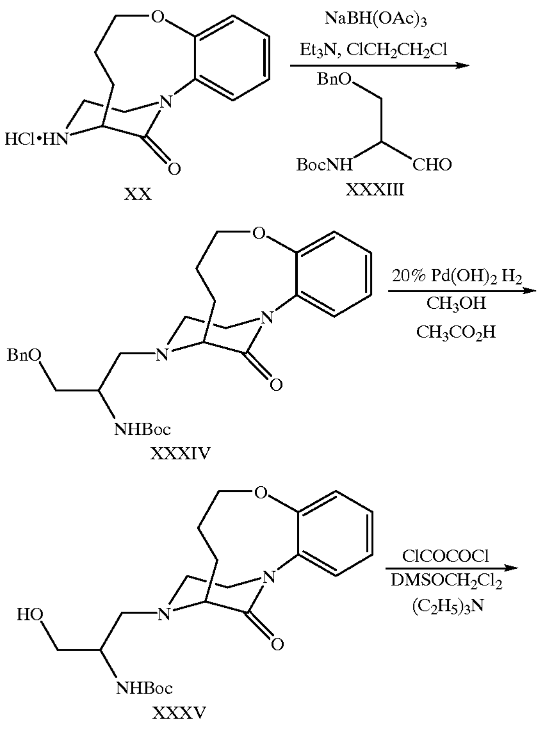
XX
XXXIII
XXXIV
XXXV
-continued
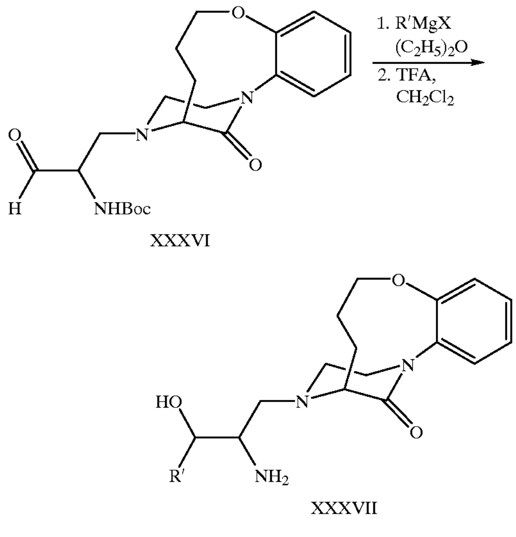
XXXVI
XXXVII
SCHEME 9
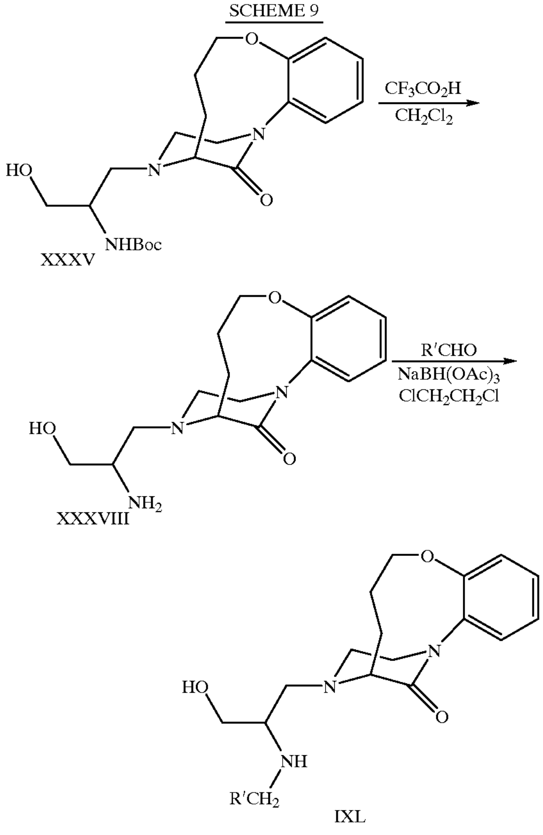
XXXV
XXXVIII
IXL SCHEME 10
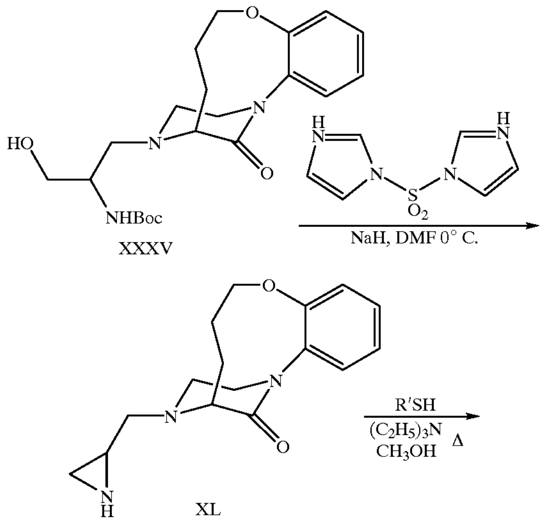
XXXV
XL
-continued
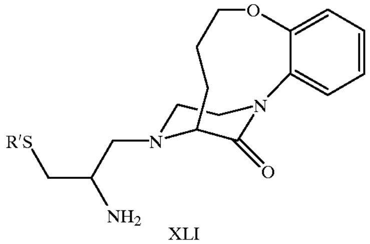
XLI
SCHEME 11
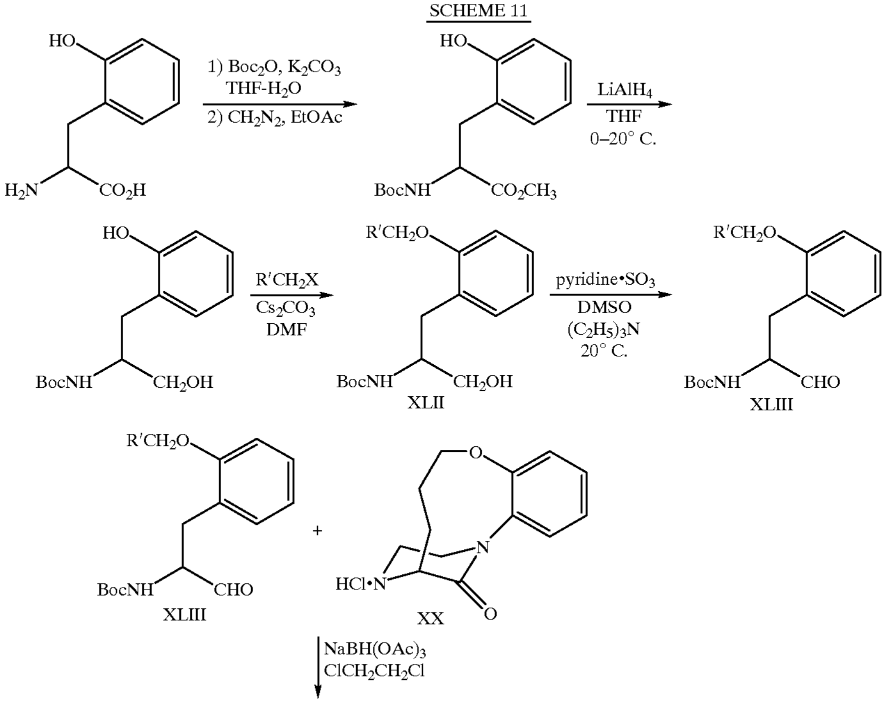
XLII
XLIII
XLIII
XX -continued
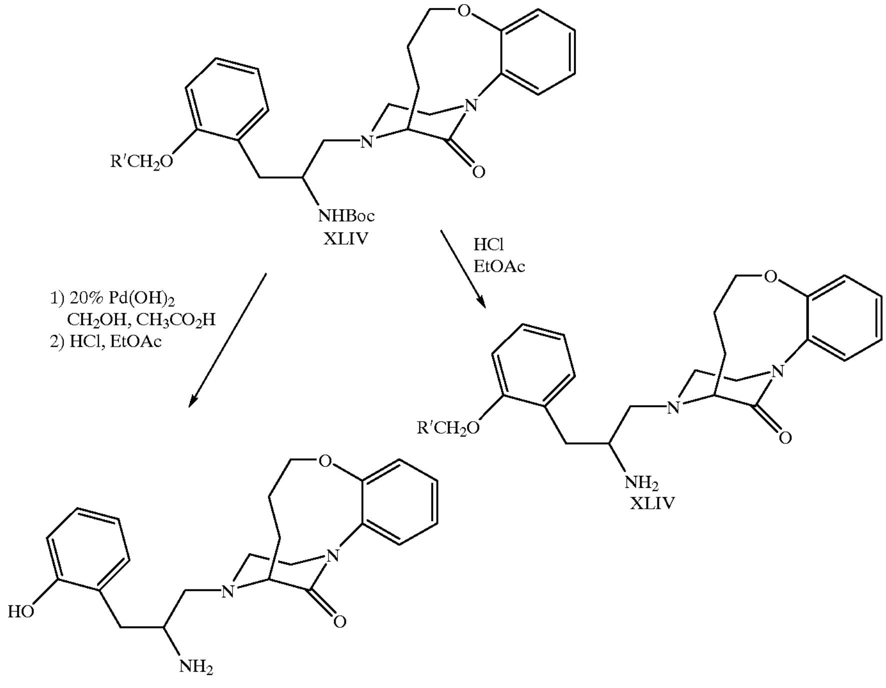
XLIV
XLIV
XLIV
REACTION SCHEME 12
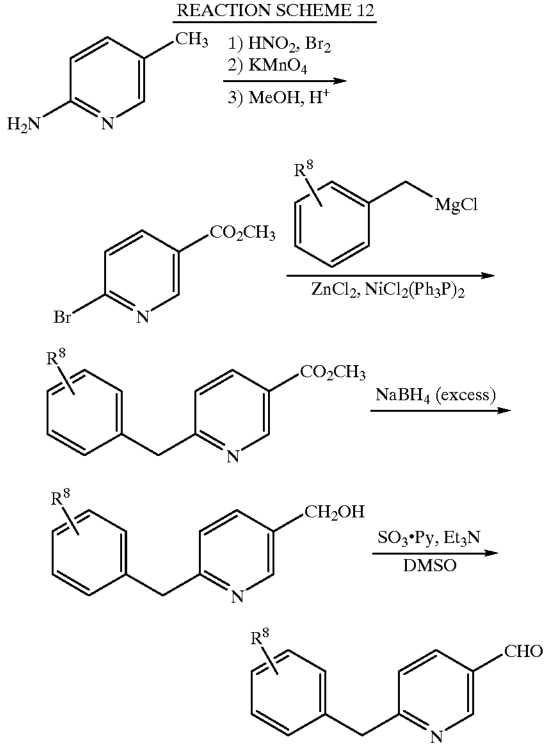
REACTION SCHEME 13
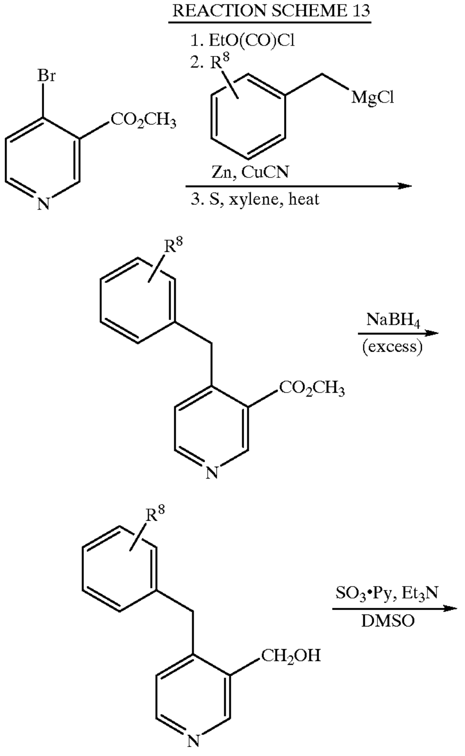

-continued
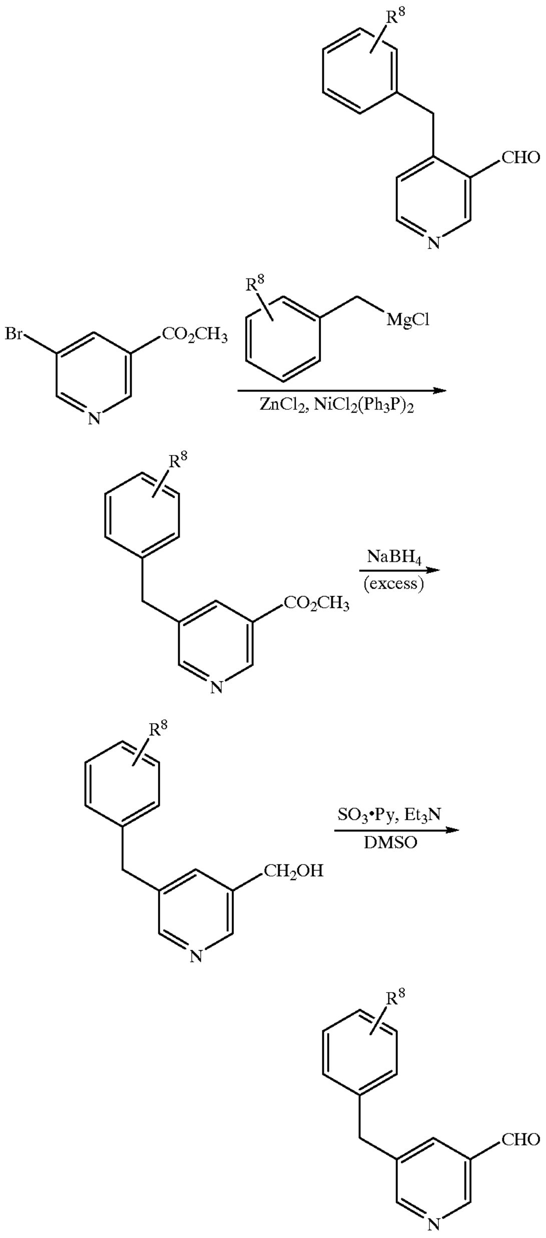
REACTION SCHEME 14
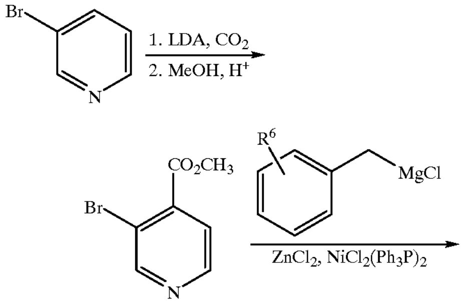
-continued
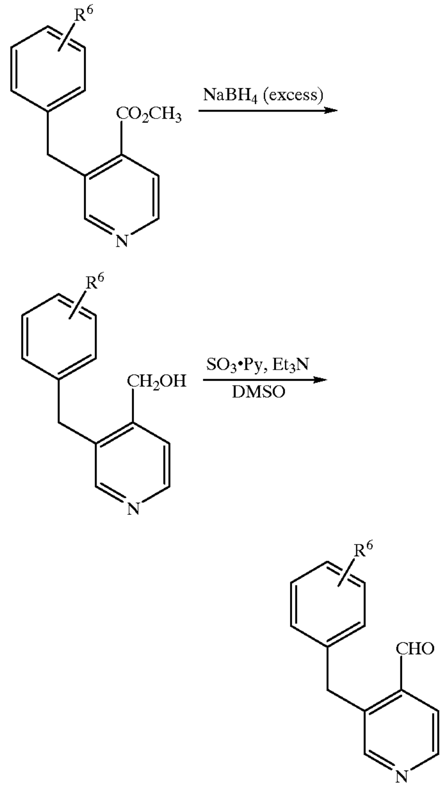
REACTION SCHEME 15
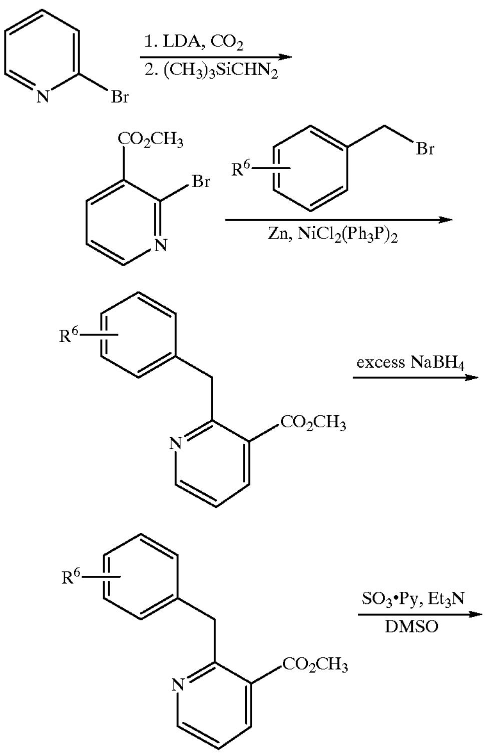

-continued

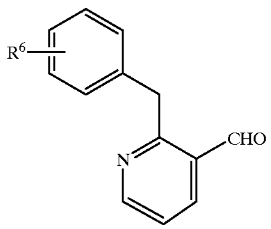

The instant compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, myeloid leukemias and neurological tumors. Such tumors may arise by mutations in the ras genes themselves, mutations in the proteins that can regulate Ras activity (i.e., neurofibromin (NF-1), neu, scr, abl, lck, fyn) or by other mechanisms.

The compounds of the instant invention inhibit farnesyl-protein transferase and the farnesylation of the oncogene protein Ras. The instant compounds may also inhibit tumor angiogenesis, thereby affecting the growth of tumors (J. Rak et al. *Cancer Research*, 55:4575–4580 (1995)). Such anti-angiogenesis properties of the instant compounds may also be useful in the treatment of certain forms of blindness related to retinal vascularization.

The compounds of this invention are also useful for inhibiting other proliferative diseases, both benign and malignant, wherein Ras proteins are aberrantly activated as a result of oncogenic mutation in other genes (i.e., the Ras gene itself is not activated by mutation to an oncogenic form) with said inhibition being accomplished by the administration of an effective amount of the compounds of the invention to a mammal in need of such treatment. For example, a component of NF-1 is a benign proliferative disorder.

The instant compounds may also be useful in the treatment of certain viral infections, in particular in the treatment of hepatitis delta and related viruses (J. S. Glenn et al. *Science*, 256:1331–1333 (1992).

The compounds of the instant invention are also useful in the prevention of restenosis after percutaneous transluminal coronary angioplasty by inhibiting neointimal formation (C. Indolfi et al. *Nature medicine*, 1:541–545(1995).

The instant compounds may also be useful in the treatment and prevention of polycystic kidney disease (D. L. Schaffner et al. *American Journal of Pathology*, 142:1051–1060 (1993) and B. Cowley, Jr. et al. *FASEB Journal*, 2:A3160 (1988)).

The instant compounds may also be useful for the treatment of fungal infections.

In a preferred embodiment of the instant invention the compounds of this instant invention are selective inhibitors of farnesyl-protein transferase. A compound is considered a selective inhibitor of farnesyl-protein transferase, for example, when its in vitro farnesyl-protein transferase inhibitory activity, as assessed by the assay described in Example 5, is at least 100 times greater than the in vitro activity of the same compound against geranylgeranyl-protein transferase-type I in the assay described in Example 6. Preferably, a selective compound exhibits at least 1000 times greater activity against one of the enzymatic activities when comparing geranylgeranyl-protein transferase-type I inhibition and farnesyl-protein transferase inhibition.

In another preferred embodiment of the instant invention the compounds of this instant invention are dual inhibitors of farnesyl-protein transferase and geranylgeranyl-protein transferase type I. Such a dual inhibitor will exhibit certain characteristics when assessed in in vitro assays, which are dependent on the type of assay employed.

In a SEAP assay, such as described in Example 9, it is preferred that the dual inhibitor compound has an in vitro inhibitory activity ($IC_{50}$) that is less than about 12 $\mu$M against K4B-Ras dependent activation of MAP kinases in cells. More preferably, the dual inhibitor compound has an in vitro inhibitory activity ($IC_{50}$) against K4B-Ras dependent activation of MAP kinases in cells which is more than about 5 times lower than the inhibitory activity ($IC_{50}$) against Myr-Ras dependent activation of MAP kinases in cells. Also more preferably, in a SEAP assay, the dual inhibitor compound has an inhibitory activity ($IC_{50}$) that is less than about 10 nM against H-Ras dependent activation of MAP kinases in cells.

In a GGTase plus anion assay, such as described in Example 6, it is preferred that the dual inhibitor compound has an in vitro inhibitory activity ($IC_{50}$) that is less than about 5 $\mu$M against transfer of a geranylgeranyl residue to a protein or peptide substrate comprising a $CAAX^G$ motif by geranylgeranyl-protein transferase type I in the presence of a modulating anion. More preferably, the dual inhibitor compound has an in vitro inhibitory activity ($IC_{50}$) that is less than about 1 $\mu$M against transfer of a geranylgeranyl residue to a protein or peptide substrate comprising a $CAAX^G$ motif by geranylgeranyl-protein transferase type I in the presence of a modulating anion. Preferably, the dual inhibitor compound has an in vitro inhibitory activity ($IC_{50}$) in the in vitro assay as described in Example 5 that is less than about 1 $\mu$M against transfer of a farnesyl residue to a protein or peptide substrate, comprising a $CAAX^F$ motif, by farnesyl-protein transferase. more preferably, the dual inhibitor compound has an in vitro inhibitory activity ($IC_{50}$) that is less than about 100 nM against transfer of a farnesyl residue to a protein or peptide substrate, comprising a $CAAX^F$ motif, by farnesyl-protein transferase. Also preferably, the dual inhibitor compound has an in vitro inhibitory activity ($IC_{50}$) in the in vitro assay as described in Example 8, that is less than about 100 nM against the anchorage independent growth of H-ras-transformed mammalian fibroblasts.

The protein or peptide substrate utilized in the instant assay may incorporate any CAAX motif that is geranylgeranylated by GGTase-I. The term "$CAAX^G$" will refer to such motifs that may be geranylgeranylated by GGTase-I. It is understood that some of the "$CAAX^G$" containing protein or peptide substrates may also be farnesylated by farnesyl-protein transferase. In particular such "$CAAX^G$" motifs include (the corresponding human protein is in parentheses): CVIM (K4B-Ras) (SEQ.ID.NO.: 1), CVLL (mutated H-Ras) (SEQ.ID.NO.: 2), CVVM (N-Ras) (SEQ.ID.NO.: 3), CIIM (K4A-Ras) (SEQ.ID.NO.: 4), CLLL (Rap-IA) (SEQ.ID.NO.: 5), CQLL (Rap-IB) (SEQ.ID.NO.: 6), CSIM (SEQ.ID.NO.: 7), CAIM (SEQ.ID.NO.: 8), CKVL (SEQ.ID.NO.: 9) and CLIM (PFX) (SEQ.ID.NO.: 10). Preferably, the CAAX motif is CVIM (SEQ.ID.NO.: 1).

As used herein, the term "$CAAX^F$" is used to designate a protein or peptide substrate that incorporates four amino acid C-terminus motif that is farnesylated by farnesyl-protein transferase. It is understood that certain of the "$CAAX^F$" containing protein or peptide substrates may also be geranylgeranylated by GGTase-I. In particular such "$CAAX^F$" motifs include (the corresponding human protein is in parentheses): CVLS (H-ras) (SEQ.ID.NO.: 11), CVIM (K4B-Ras) (SEQ.ID.NO.: 1) and CVVM (N-Ras) (SEQ.ID.NO.: 3).

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

For oral use of a chemotherapeutic compound according to this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the instant invention may also be co-administered with other well known therapeutic agents that are selected for their particular usefulness against the condition that is being treated. For example, the instant compounds may be useful in combination with known anti-cancer and cytotoxic agents. Similarly, the instant compounds may be useful in combination with agents that are effective in the treatment and prevention of NF-1, restinosis, polycystic kidney disease, infections of hepatitis delta and related viruses and fungal infections.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patients blood-stream by local bolus injection.

As used herein, the term "composition" is intended to encompass a product comprising the specified ingredients in the specific amounts, as well as any product which results, directly or indirectly, from combination of the specific ingredients in the specified amounts.

The compositions of the instant invention may alternatively or in addition comprise a farnesyl pyrophosphate-competitive inhibitor. In particular, the compounds disclosed in the following patents and publications may be useful as farnesyl pyrophosphate-competitive inhibitor component of the instant composition: U.S. Ser. Nos. 08/254,228 and 081435,047.

In practicing methods of this invention, which comprise administering, simultaneously or sequentially or in any order, two or more of a protein substrate-competitive inhibitor and a farnesyl pyrophosphate-competitive inhibitor, such administration can be orally or parenterally, including intravenous, intramuscular, intraperitoneal, subcutaneous, rectal and topical routes of administration. It is preferred that such administration be orally. It is more preferred that such administration be orally and simultaneously. When the protein substrate-competitive inhibitor and farnesyl pyrophosphate-competitive inhibitor are administered sequentially, the administration of each can be by the same method or by different methods.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of the instant invention are also useful as a component in an assay to rapidly determine the presence and quantity of farnesyl-protein transferase (FPTase) in a composition. Thus the composition to be tested may be divided and the two portions contacted with mixtures which comprise a known substrate of FPTase (for example a tetrapeptide having a cysteine at the amine terminus) and farnesyl pyrophosphate and, in one of the mixtures, a compound of the instant invention. After the assay mixtures are incubated for an sufficient period of time, well known in the art, to allow the FPTase to farnesylate the substrate, the chemical content of the assay mixtures may be determined by well known immunological, radiochemical or chromatographic techniques. Because the compounds of the instant invention are selective inhibitors of FPTase, absence or quantitative reduction of the amount of substrate in the assay mixture without the compound of the instant invention relative to the presence of the unchanged substrate in the assay containing the instant compound is indicative of the presence of FPTase in the composition to be tested.

It would be readily apparent to one of ordinary skill in the art that such an assay as described above would be useful in identifying tissue samples which contain farnesyl-protein transferase and quantitating the enzyme. Thus, potent inhibitor compounds of the instant invention may be used in an active site titration assay to determine the quantity of enzyme in the sample. A series of samples composed of aliquots of a tissue extract containing an unknown amount of farnesyl-protein transferase, an excess amount of a known substrate of FPTase (for example a tetrapeptide having a cysteine at the amine terminus) and farnesyl pyrophosphate are incubated for an appropriate period of time in the presence of varying concentrations of a compound of the instant invention. The concentration of a sufficiently potent inhibitor (i.e., one that has a Ki substantially smaller than the concentration of enzyme in the assay vessel) required to inhibit the enzymatic activity of the sample by 50% is approximately equal to half of the concentration of the enzyme in that particular sample.

EXAMPLES

Examples provided are intended to assist in a further understanding of the invention. Particular materials employed, species and conditions are intended to be further illustrative of the invention and not limitative of the reasonable scope thereof.

Example 1

Preparation of 1(R),5(S)-3-[(3-trifluoromethyl)phenyl]-8-[(4-cyanobenzyl)-5-imidazolylmethyl]-3,8-diaza-2-oxobicyclo[3.2.1 ]octane dihydrochloride Step A: Preparation of 1-triphenylmethyl-4-(hydroxymethyl)-imidazole To a solution of 4-(hydroxymethyl)imidazole hydrochloride (35.0 g, 260 mmol) in 250 mL of dry DMF at room temperature was added triethylamine (90.6 mL, 650 mmol). A white solid precipitated from the solution. Chlorotriphenylmethane (76.1 g, 273 mmol) in 500 mL of DMF was added dropwise. The reaction mixture was stirred for 20 hours, poured over ice, filtered, and washed with ice water. The resulting product was slurried with cold dioxane, filtered, and dried in vacuo to provide the titled product as a white solid which was sufficiently pure for use in the next step.

Step B: Preparation of 1-triphenylmethyl-4-(acetoxymethyl)-imidazole

Alcohol described in Step A (260 mmol, prepared above) was suspended in 500 mL of pyridine. Acetic anhydride (74 mL, 780 mmol) was added dropwise, and the reaction was stirred for 48 hours during which it became homogeneous. The solution was poured into 2 L of EtOAc, washed with water (3×1 L), 5% aqueous HCl solution (2×1 L), saturated aqueous $NaHCO_3$, and brine, then dried ($Na_2SO_4$), filtered, and concentrated in vacuo to provide the crude product. The acetate was isolated as a white powder which was sufficiently pure for use in the next reaction.

Step C: Preparation of 1-(4-cyanobenzyl)-5-(acetoxymethyl)-imidazole hydrobromide A solution of the product described in Step B (85.8 g, 225 mmol) and α-bromo-p-tolunitrile (50.1 g, 232 mmol) in 500 mL of EtOAc was stirred at 60° C. for 20 hours, during which a pale yellow precipitate formed. The reaction was cooled to room temperature and filtered to provide the solid imidazolium bromide salt. The filtrate was concentrated in vacuo to a volume of 200 mL, reheated at 60° C. for two hours, cooled to room temperature, and filtered again. The filtrate was concentrated in vacuo to a volume of 100 mL, reheated at 60° C. for another two hours, cooled to room temperature, and concentrated in vacuo to provide a pale yellow solid. All of the solid material was combined, dissolved in 500 mL of methanol, and warmed to 60° C. After two hours, the solution was reconcentrated in vacuo to provide a white solid which was triturated with hexane to remove soluble materials. Removal of residual solvents in vacuo provided the titled product hydrobromide as a white solid which was used in the next step without further purification.

Step D: Preparation of 1-(4-cyanobenzyl)-5-(hydroxymethyl)-imidazole

To a solution of the acetate described in Step C (50.4 g, 150 mmol) in 1.5 L of 3:1 THF/water at 0° C. was added lithium hydroxide monohydrate (18.9 g, 450 mmol). After one hour, the reaction was concentrated in vacuo, diluted with EtOAc (3 L), and washed with water, saturated aqueous $NaHCO_3$ and brine. The solution was then dried ($Na_2SO_4$), filtered, and concentrated in vacuo to provide the crude product as a pale yellow fluffy solid which was sufficiently pure for use in the next step without further purification.

Step E: Preparation of 1-(4-cyanobenzyl)-5-imidazole carboxaldehyde

To a solution of the alcohol described in Step D (21.5 g, 101 mmol) in 500 mL of DMSO at room temperature was added triethylamine (56 mL, 402 mmol), then $SO_3$-pyridine complex (40.5 g, 254 mmol). After 45 minutes, the reaction was poured into 2.5 L of EtOAc, washed with water (4×1 L) and brine, dried ($Na_2SO_4$), filtered, and concentrated in vacuo to provide the aldehyde as a white powder which was sufficiently pure for use in the next step without further purification.

Step F: Preparation of (S)-4-(tert-butoxycarbonyl)-5-(2-hydroxyethyl)-1-(3-trifluoromethylphenyl)piperazin-2-one The titled compound was prepared from (S)-4-benzyloxy-N-(tert-butoxycarbonyl)butanoic acid and 3-(trifluoromethyl)aniline in direct analogy to the procedures found in Example 41 of the PCT application WO 96/30343. Thus, (S)-4-benzyloxy-N-(tert-butoxycarbonyl) butanoic acid was converted to the corresponding N-methoxy-N-methyl amide, reduced to the corresponding aldehyde with $LiAlH_4$, reductively alkylated to 3-(trifluoromethyl)aniline using $Na(AcO)_3BH$, N-acylated with chloroacetylchloride, and cyclized using $Cs_2CO_3$ to provide the titled piperazinone.

Step G: Preparation of (S)-4-(tert-butoxycarbonyl)-5-[2-(methanesulfonyloxy)ethyl]-1-(3-trifluoromethylphenyl) piperazin-2-one To a solution of the alcohol described in Step F (102 mg, 0.263 mmol) in 1.0 mL of methylene chloride at 0° C. was added N,N-dilsopropylethylamine (0.093 mL, 0.53 mmol), followed by methanesulfonyl chloride (0.025 mL, 0.32 mmol). After two hours, the solution was poured into ethyl acetate, washed with saturated $NH_4Cl$ solution, saturated $NaHCO_3$ solution, and brine. The resulting solution was dried with sodium sulfate, filtered, and concentrated in vacuo to provide the titled compound.

Step H: Preparation of 1 (R),5(S)-8-(tert-butoxycarbonyl)-3-[(3-trifluoromethyl)phenyl]-3,8-diaza-2-oxobicyclo [3.2.1]octane To a solution of the mesylate described in Step G (106 mg, 0.227 mmol) in 2.0 mL of THF at −78° C. was added dropwise 1M lithium hexamethyldisilazide in THF solution (0.250 mL, 0.250 mmol). The solution was allowed to warm to room temperature and stir for an additional 30 minutes. After HPLC analysis showed incomplete conversion, the solution was recooled to −78° C., and an additional portion of lithium hexamethyldisilazide solution (0.200 mL, 0.200 mmol) was added dropwise. The solution was stirred for one hour, allowed to warm to room temperature, and stirred for an additional two hours. The reaction was poured into ethyl acetate, washed with saturated $NH_4Cl$ solution, saturated $NaHCO_3$ solution, and brine. The resulting solution was dried with sodium sulfate, filtered, and concentrated in vacuo to provide the titled compound which was used in the next reaction without further purification.

Step I: Preparation of 1(R),5(S)-3-[(3-trifluoromethyl) phenyl]-3,8-diaza-2-oxobicyclo[3.2.1]octane hydrochloride Through a solution of the product described in Step H (93 mg, theoretically 0.227 mmol) in 3.0 mL of ethyl acetate at 0° C. was bubbled anhydrous HCl gas for one hour. The solution was concentrated in vacuo to provide the titled salt as a brown foam which was used in the next reaction without further purification.

Step J: Preparation of 1(R),5(S)-3-[(3-trifluoromethyl) phenyl]-8-[(4-cyanobenzyl)-5-imidazolylmethyl]-3,8-diaza-2-oxobicyclo[3.2.1]octane dihydrochloride To a solution of the amine described in Step 1 (81 mg, theoretically 0.227 mmol) in 2 mL of 1,2-dichloroethane at 0° C. was added 4 Å powdered molecular sieves (200 mg), followed by sodium triacetoxyborohydride (100 mg, 0.47 mmol). The aldehyde described in Step E (76 mg, 0.36 mmol) was added, and the reaction was allowed to warm to room temperature. After 24 hours, the reaction was poured into EtOAc, washed with saturated aqueous $NaHCO_3$ and brine, dried ($Na_2SO_4$), filtered, and concentrated in vacuo. The resulting product was purified by silica gel chromatography (50–80% acetone/$CH_2Cl_2$), taken up in $CH_2Cl_2$ and treated with excess 1 M HCl/ether solution, and concentrated in vacuo to provide the titled product hydrochloride as a white powder.

FAB mass spectrum m/e 466.21 (M+1). Analysis calculated for $C_{25}H_{22}F_3N_5O$•3.0 HCl•0.10 $H_2O$: C, 52.07; H, 4.40; N, 12.14; Found: C, 52.09; H, 4.42; N, 11.72.

Example 2

Preparation of (±)-9-[1-(4-cyanobenzyl)-5-imidazolylmethyl]-b-benzo-1,9-diaza-4-oxa-12-oxobicyclo [6.3.1]dodecane dihydrochloride Step A: Preparation 2-[(3,4-dichlorobenzyl)oxy] nitrobenzene A solution of 3,4-dichlorobenzyl alcohol (25.0 g, 141 mmol), 2-fluorobenzaldehyde (14.9 mL, 141 mmol) and potassium carbonate (39.0 g, 282 mmol) in 100 mL of dry DMF was stirred a 60° C. overnight. The DMF was removed in vacuo, and the resulting product was taken up in EtOAc/water. The organic phase was washed with brine, dried ($Na_2SO_4$), filtered, and concentrated in vacuo to provide the titled compound which was used in the next reaction without further purification.

Step B: Preparation 2-[(3,4-dichlorobenzyl)oxy]aniline hydrochloride

A solution of the product described in Step A (39.5 g, 132 mmol), iron filings (26 g, 462 mmol) and acetic acid (57 mL) in 250 mL of methanol was heated to reflux. After 3.5 hours, the solution was cooled, filtered, and the filter cake was washed with methanol. The filtrate was concentrated in vacuo, taken up in EtOAc, and washed with saturated $NaHCO_3$ solution and brine. The resulting solution was dried with sodium sulfate, filtered, and concentrated in vacuo to provide 32 g of the aniline product. This was dissolved in 100 mL methylene choloride, and dry HCl gas was bubbled through the solution at 0° C. Concentration in vacuo provided the titled compound.

Step C: Preparation of N-[2-((3,4-dichlorobenzyl)-oxy) phenyl]ethylenediamine

A solution of the aniline hydrochloride described in Step B (30.0 g, 98.5 mmol) and 2-oxazolidinone (8.6 g, 98.5 mmol) in 30 mL of 2-(2-methoxyethoxy)ethanol was heated to 160° C. for 3.5 hours, during which gas evolution was observed. The reaction was cooled, then filtered, then partitioned between EtOAc and aqueous $NaHCO_3$. After washing with brine, the solution was concentrated in vaciuo. The resulting product was purified by silica gel chromatography (95:5:0.5-90:10:1; $CHCl_3$/MeOH/$NH_4OH$) to provide the titled compound.

Step D: Preparation of N-(tert-butoxycarbonyl)-N'[2-((3,4-dichlorobenzyl)-oxy)phenyl]ethylenediamine The product described in Step C (20.8 g, 66.8 mmol) was taken up in 50 mL of THF and 50 mL of saturated aqueous $NaHCO_3$ solution, and cooled to 0° C. Di-tert-butylpyrocarbonate (14.6 g, 66.8 mmol) was added, and the solution was allowed to warm to room temperature. After 3.5 h, the reaction was poured into EtOAc, washed with water and brine, dried ($Na_2SO_4$), filtered, and concentrated in vacuo to provide the titled carbamate which was used in the next step without further purification.

Step E: Preparation of N-[2-(tert-butoxycarbamoyl)ethyl]-N'-[2-((3,4-dichlorobenzyl)-oxy)phenyl]-2-chloroacetamide The product described in Step D (20.3 g, 49.4 mmol) was taken up in 150 mL of THF and 100 mL of saturated aqueous $NaHCO_3$ solution, and cooled to 0° C. Chloroacetylchloride (4.4 mL, 54.4 mmol) was added dropwise, and the solution was stirred for two hours. Another 100 mL of sat $NaHCO_3$ and 50 mL EtOAc were added, followed by an additional portion of chloroacetylchloride (1.0 mL). After 1.5 h, the reaction was poured into EtOAc, washed with water and brine, dried ($Na_2SO_4$), filtered, and concentrated in vacuo to provide the crude solid product, which was re-precipitated from ether/hexane and filtered to provide the titled product which was used in the next step without further purification.

Step F: Preparation of 4-(tert-butoxycarbonyl)-1-[2-((3,4-dichlorobenzyl)-oxy)phenyl]-2-piperazinone To a solution of the chloroacetamide described in Step E (12.4 g, 25.4 mmol) in 75 mL of dry DMF was added $Cs_2CO_3$ (24.4 g, 75 mmol). The solution was heated in an oil bath at 45° C. for 3.5 hours, cooled to room temperature, poured into EtOAc/water. The organic phase was washed with water and brine, dried ($Na_2SO_4$), filtered, and concentrated in vacuo to provide the titled product which was used in the next step without further purification.

Step G: Preparation of 4-(tert-butoxycarbonyl)-1-(2-hydroxyphenyl)-2-piperazinone To a solution of the piperazinone described in Step F (2.00 g, 4.43 mmol) in 25 mL of methylene chloride was added sodium iodide (2.0 g, 13.3 mmol), and the solution was cooled to −15° C. Solid AlBr3 was added (2.4 g, 8.9 mmol), and the solution was allowed to warm to room temperature and stir overnight. The reaction was diluted with 25 mL methylene chloride and 50 mL saturated NaHCO3 solution, and di-tert-butylpyrocarbonate (1.95 g, 8.9 mmol) was added at room temperature. After 5 hours, the layers were seperated, the aqueous phase was extracted with EtOAc, and the combined organics were dried ($Na_2SO_4$), filtered, and concentrated in vacuo. The resulting product was purified by silica gel chromatography (25–100% EtOAc/hexane) to provide the titled compound.

Step H: Preparation of 4-(tert-butoxycarbonyl)-1-[2-((3-chloropropyl)oxy)phenyl]-2-piperazinone To a solution of the phenol described in Step G (388 mg, 1.33 mmol) in 7 mL of dry DMF was added 1-chloro-3-iodopropane (0.161 mL, 1.5 mmol) and $Cs_2CO_3$ (706 mg, 2.0 mmol). The reaction was stirred at room temperature for 3 hours, then poured into EtOAc and washed with water, saturated $NaHCO_3$, and brine. The solution was dried ($Na_2SO_4$), filtered, and concentrated in vacuo to provide the titled product which was used in the next step without further purification.

Step I: Preparation of 4-(tert-butoxycarbonyl)-1-[2-((3-iodopropyl)oxy)phenyl]-2-piperazinone To a solution of the chloride described in Step H (436 mg, 1.18 mmol) in 10 mL of acetone was added sodium iodide (1.8 g, 12 mmol). The solution was refluxed for 3 hours, then allowed to cool to room temperature overnight. The reaction was diluted with EtOAc, washed with water and brine, dried ($Na_2SO_4$), filtered, and concentrated in vacuo. The resulting product was purified by silica gel chromatography (40% EtOAc/hexane) to provide the titled compound.

Step J: Preparation of (±)-9-(tert-butoxycarbonyl)-b-benzo-1,9-diaza-4-oxa-12-oxobicyclo[6.3.1]dodecane To a solution of the iodide described in Step I (300 mg, 0.65 mmol) in 11 mL of THF at −78° C. was added dropwise 1M lithium hexamethyldisilazide in THF solution (1.43 mL, 1.43 mmol). The reaction was allowed to warm to room temperature over 1.5 hours, then poured into ethyl acetate, washed with saturated $NaHCO_3$ solution, and brine. The resulting solution was dried with sodium sulfate, filtered, and concentrated in vacuo to provide the titled compound which was used in the next reaction without further purification.

Step K: Preparation of (±)-b-benzo-1,9-diaza-4-oxa-12-oxobicyclo[6.3.1]dodecane hydrochloride Through a solution of the product described in Step J (292 mg, 0.88 mmol) in 10.0 mL of ethyl acetate at 0° C. was bubbled anhydrous HCl gas for 5 minutes. After stirring for an additional 30 minutes, the solution was concentrated in vacuo to provide the titled salt as a brown foam which was used in the next reaction without further purification.

Step L: Preparation of (±)-9-[1-(4-cyanobenzyl)-5-imidazolylmethyl]-b-benzo-1,9-diaza-4-oxa-12-oxobicyclo [6.3.1]dodecane dihydrochloride To a solution of the amine hydrochloride described in Step K (237 mg, 0.88 mmol) in 6 mL of 1,2-dichloroethane at 0° C. was added 4 Å powdered molecular sieves (1.5 g), followed by sodium triacetoxyborohydride (280 mg, 1.32 mmol). The aldehyde described in Step E of Example 1 (186 mg, 0.88 mmol) was added, and the reaction was allowed to warm to room temperature. After 24 hours, the reaction was poured into EtOAc, washed with saturated aqueous $NaHCO_3$ and brine, dried ($Na_2SO_4$), filtered, and concentrated in vacuo. The residue was stirred in a solution of 10 mL of methylene chloride and 6 mL of n-propylamine for 2 hours, then concentrated in vacuo. The resulting product was purified by silica gel chromatography (50–80% acetone/$CH_2Cl_2$), taken up in $CH_2Cl_2$ and treated with excess 1 M HCl/ether solution, and concentrated in vacuo to provide the titled product hydrochloride as a white powder.

FAB mass spectrum m/e 428 (M+1). Analysis calculated for $C_{25}H_{25}N_5O2$•2.0 HCl•0.30 CHCl3•1.0 $H_2O$: C, 54.83; H, 5.33; N, 12.64; Found: C, 54.88; H, 5.37; N, 11.80.

Example 3

Preparation of (±)-9-[1-(4-cyanobenzyl)-5-imidazolylmethyl]-1,9-diaza-b,e-dibenzo-4-oxa-12-oxobicyclo[6.3.1]dodecane dihydrochloride Step A: Preparation of 4-(tert-butoxycarbonyl)-1-[2-((2-formylphenyl)oxy)phenyl]-2-piperazinone To a solution of the phenol described in Step G of Example 2 (395 mg, 1.35 mmol) in 4 mL of dry DMF was added 2-fluorobenzaldehyde (0.145 mL, 1.35 mmol) and $K_2CO_3$ (372 mg, 2.70 mmol). The reaction was stirred at 70° C. for 48 hours, then poured into EtOAc and washed with water, saturated $NaHCO_3$, and brine. The solution was dried ($Na_2SO_4$), filtered, and concentrated in vacuo to provide the titled product which was used in the next step without further purification.

Step B: Preparation of 4-(tert-butoxycarbonyl)-1-[2-((2-hydroxymethylphenyl)oxy)phenyl]-2-piperazinone To a solution of the aldehyde described in Step A (456 mg, 1.15 mmol) in 5 mL of ethanol was added sodium borohydride (88 mg, 2.3 mmol) at room temperature. After 45 minutes, the reaction was quenched with saturated $NH_4Cl$ solution, then poured into EtOAc and washed with saturated $NaHCO_3$, and brine. The solution was dried ($Na_2SO_4$), filtered, and concentrated in vacuo to provide the titled product which was used in the next step without further purification.

Step C: Preparation of 4-(tert-butoxycarbonyl)-1-[2-((2-methanesulfonyloxymethylphenyl)oxy)phenyl3-2-piperazinone To a solution of the alcohol described in Step B (105 mg, 0.264 mmol) in 2 mL of methylene chloride at 0° C. was added triethylamine (0.074 mL. 0.58 mmol), followed by methanesulfonic anhydride (50.5 mg, 0.289 mmol). After 15 minutes, the reaction was poured into EtOAc and washed with saturated $NaHCO_3$, and brine. The solution was dried ($Na_2SO_4$), filtered, and concentrated in vacuo. The resulting product was purified by silica gel chromatography (50–70% EtOAc/hexane) to provide the titled product as a yellow solid.

Step D: Preparation of (±)-9-(tert-butoxycarbonyl)-1,9-diaza-b,e-dibenzo-4-oxa-12-oxobicyclo[6.3.1]dodecane To a solution of the mesylate described in Step C (61 mg, 0.128 mmol) in 1.0 mL of THF at −78° C. was added dropwise 1M lithium hexamethyldisilazide in THF solution (0.192 mL, 0.192 mmol). The reaction was allowed to warm to room temperature over 45 minutes, then poured into ethyl acetate, washed with saturated $NaHCO_3$ solution, and brine. The resulting solution was dried with sodium sulfate, filtered, and concentrated in vacuo. The resulting product was purified by silica gel chromatography (50% EtOAc/hexane) to provide the titled product as a white foam.

Step E: Preparation of (±)-1,9-diaza-b,e-dibenzo-4-oxa-12-oxobicyclo[6.3.1]dodecane hydrochloride Through a solution of the product described in Step D (21.6 mg, 0.054 mmol) in 2.0 mL of ethyl acetate at 0° C. was bubbled anhydrous HCl gas for 15 minutes. After stirring for an additional 45 minutes, the solution was concentrated in vacuo to provide the titled salt as a white solid which was used in the next reaction without further purification.

Step F: Preparation of (±)-9-[1-(4-cyanobenzyl)-5-imidazolylmethyl]-1,9-diaza-b,e-dibenzo-4-oxa-12-oxobicyclo[6.3.1]dodecane dihydrochloride To a solution of the amine hydrochloride described in Step E (ca. 0.054 mmol) in 1 mL of 1,2-dichloroethane at 0° C. was added 4Å powdered molecular sieves (50 mg), followed by sodium triacetoxyborohydride (28 mg, 0.13 mmol). The aldehyde described in Step E of Example 1 (15 mg, 0.071 mmol) was added, and the reaction was allowed to warm to room temperature. After 16 hours, the reaction was poured into EtOAc, washed with saturated aqueous $NaHCO_3$ and brine, dried ($Na_2SO_4$), filtered, and concentrated in vacuo. The residue was stirred in a solution of 25% n-propylamine/methylene chloride for 2 hours, then concentrated in vacuo. The resulting product was purified by silica gel chromatography (35–50% acetone/$CH_2Cl_2$), taken up in $CH_2Cl_2$ and treated with excess 1 M HCl/ether solution, and concentrated in vacuo to provide the titled product hydrochloride as a white powder.

FAB mass spectrum m/e 476 (M+1). Analysis calculated for $C_{29}H_{25}N_5O2$•2.20 HCl•1.20 $H_2O$: C, 60.33; H, 5.17; N, 12.13; Found: C, 60.29; H, 5.15; N, 11.64.

Example 4

Preparation of (±)-9-[1-(4-cyanobenzyl)-5-imidazolylcarbonyl]-1,9-diaza-b,e-dibenzo-4-oxa-bicyclo [6.3.1]dodecane hydrochloride Step A: Preparation of 1-(4-cyanobenzyl)-5-imidazolecarboxylic acid sodium salt To a solution of $NaClO_2$ (65 mg, 0.58 mmol) and NaH2PO4 (67 mg, 0.49 mmol) in 1 mL of water was added a solution of the aldehyde described in Step E of Example 1 (100 mg, 0.487 mmol) and 2-methyl-2-butene (1 mL) in 5 mL of tert-butanol. The clear solution gradually turned pale yellow, and a white precipitate formed. After 2 hours, the solution was filtered, and the solid material was dried in vacuo to provide the carboxylate salt as a white powder which was sufficiently pure for use in the next step without further purification.

Step B: Preparation of (±)-1,9-diaza-b,e-dibenzo-4-oxabicyclol6.3.1]dodecane

To a solution of the amine hydrochloride described in Step E of Example 3 (80.1 mg, 0.253 mmol) in 2.0 mL of THF at room temperature was added lithium aluminum hydride (23 mg, 0.60 mmol). The reaction was stirred for 16 hours, then quenched with 10% Hcl solution and stirred for 30 minutes. The solution was poured into ethyl acetate, washed with saturated $NaHCO_3$ solution, and brine, dried ($Na_2SO_4$), filtered, and concentrated in vacuo to provide the titled product as a pale yellow foam which was used in the next reaction without further purification.

Step C: Preparation of (±)-9-[1-(4-cyanobenzyl)-5-imidazolylcarbonyl]-1,9-diaza-b, e-dibenzo-4 -oxabicyclo [6.3.1]dodecane hydrochloride To a solution of the amine described in Step B (61.7 mg, 0.232 mmol) in 1 mL of DMF at room temperature was added the carboxylic acid sodium salt described in Step A (104 mg, 0.42 mmol), HOBt•$H_2O$ (43 mg, 0.32 mmol), and EDC•HCl (67 mg, 0.35 mmol). The reaction was stirred at room temperature overnight, then poured into EtOAc, washed with saturated aqueous $NaHCO_3$ and brine, dried ($Na_2SO_4$), filtered, and concentrated in vacuo. The residue was purified by silica gel chromatography (50–90% acetone/$CH_2Cl_2$), taken up in $CH_2Cl_2$ and treated with excess 1 M HCl/ether solution, and concentrated in vacuo to provide the titled product hydrochloride as a pale yellow solid.

FAB mass spectrum m/e 476 (M+1). Analysis calculated for $C_{29}H_{25}N_5O2$•2.20 HCl•2.30 $H_2O$: C, 62.12; H, 5.54; N, 12.49; Found: C, 62.05; H, 5.56; N, 11.25.

Example 5

In Vitro Inhibition of Ras Farnesyl Transferase

Assays offarnesyl-protein transferase. Partially purified bovine FPTase and Ras peptides (Ras-CVLS, Ras-CVIM and Ras-CAIL (SEQ.ID.NO.: 12) were prepared as described by Schaber et al., *J. Biol. Chem.* 265:14701–14704 (1990), Pompliano, et al., *Biochemistry* 31:3800 (1992) and Gibbs et al., *PNAS* U.S.A. 86:6630–6634 (1989), respectively. Bovine FPTase was assayed in a volume of 100 ml containing 100 mM N-(2-hydroxy ethyl) piperazine-N'-(2-ethane sulfonic acid) (HEPES), pH 7.4, 5 mM $MgCl_2$, 5 mM dithiothreitol (DTT), 100 mM [$^3$H]-farnesyl diphosphate ([$^3$H]-FPP; 740 CBq/mmol, New England Nuclear), 650 nM Ras-CVLS and 10 mg/ml FPTase at 31° C. for 60 min. Reactions were initiated with FPTase and stopped with 1 ml of 1.0 M HCL in ethanol. Precipitates were collected onto filter-mats using a TomTec Mach II cell harvestor, washed with 100% ethanol, dried and counted in an LKB b-plate counter. The assay was linear with respect to both substrates, FPTase levels and time; less than 10% of the [$^3$H]-FPP was utilized during the reaction period. Purified compounds were dissolved in 100% dimethyl sulfoxide (DMSO) and were diluted 20-fold into the assay. Percentage inhibition is measured by the amount of incorporation of radioactivity in the presence of the test compound when compared to the amount of incorporation in the absence of the test compound.

Human FPTase was prepared as described by Omer et al., *Biochemistry* 32:5167–5176 (1993). Human FPTase activity was assayed as described above with the exception that 0.1% (w/v) polyethylene glycol 20,000, 10 mM $ZnCl_2$ and 100 nM Ras-CVIM were added to the reaction mixture. Reactions were performed for 30 min., stopped with 100 ml of 30% (v/v) trichloroacetic acid (TCA) in ethanol and processed as described above for the bovine enzyme.

The compounds of the instant invention described in the above Examples were tested for inhibitory activity against human FPTase by the assay described above and were found to have $IC_{50}$ of <50 $\mu$M.

Example 6

Modified In Vitro GGTase Inhibition Asssay

The modified geranylgeranyl-protein transferase inhibition assay is carried out at room temperature. A typical reaction contains (in a final volume of 50 mL): [$^3$H] geranylgeranyl diphosphate, biotinylated Ras peptide, 50 mM HEPES, pH 7.5, a modulating anion (for example 10 mM glycerophosphate or 5 mM ATP), 5 mM $MgCl_2$, 10 mM $ZnCl_2$, 0.1% PEG (15–20,000), 2 mM dithiothreitol, and geranylgeranyl-protein transferase type I(GGTase). The GGTase-type I enzyme employed in the assay is prepared as described in U.S. Pat. No. 5,470,832, incorporated by reference. The Ras peptide is derived from the K4B-Ras protein and has the following sequence: biotinyl-GKKKKKKSKTKCVIM (single amino acid code) (SEQ.ID.NO.: 13). Reactions are initiated by the addition of GGTase and stopped at timed intervals (typically 15 min) by the addition of 200 mL of a 3 mg/mL suspension of streptavidin SPA beads (Scintillation Proximity Assay beads, Amersham) in 0.2 M sodium phosphate, pH 4, containing 50 mM EDTA, and 0.5% BSA. The quenched reactions are allowed to stand for 2 hours before analysis on a Packard TopCount scintillation counter.

For inhibition studies, assays are run as described above, except inhibitors are prepared as concentrated solutions in 100% dimethyl sulfoxide and then diluted 25-fold into the enzyme assay mixture. $IC_{50}$ values are determined with Ras peptide near $K_M$ concentrations. Enzyme and nonsaturating substrate conditions for inhibitor $IC_{50}$ determinations are as follows: 75 pM GGTase-I, 1.6 mM Ras peptide, 100 nM geranylgeranyl diphosphate.

Example 7

Cell-based in Vitro Ras Prenylation Assay

The cell lines used in this assay consist of either Rat1 or NIH3T3 cells transformed by either viral H-ras; an N-ras chimeric gene in which the C-terminal hypervariable region of viral-H-ras was substituted with the corresponding region from the N-ras gene; or ras-CVLL, a viral-H-ras mutant in which the C-terminal exon encodes leucine instead of serine, making the encoded protein a substrate for geranylgeranylation by GGTase-I. The assay can also be performed using cell lines transformed with human H-ras, N-ras or K4B-ras. The assay is performed essentially as described in DeClue, J. E. et al., Cancer Research 51:712–717, (1991). Cells in 10 cm dishes at 50–75% confluency are treated with the test compound(s) (final concentration of solvent, methanol or dimethyl sulfoxide, is 0.1 %). After 4 hours at 37° C., the cells are labelled in 3 ml methionine-free DMEM supplemented with 10% regular DMEM, 2% fetal bovine serum, 400 mCi[$^{35}$S]methionine (1000 Ci/mmol) and test compound(s). Cells treated with lovastatin, a compound that blocks Ras processing in cells by inhibiting the rate-limiting step in the isoprenoid biosynthetic pathway (Hancock, J. F. et al. *Cell*, 57:1167 (1989); DeClue, J. E. et al. *Cancer Res.*, 51:712 (1991); Sinensky, M. et al. *J. Biol. Chem.*, 265:19937 (1990)), serve as a positive control in this assay. After an additional 20 hours, the cells are lysed in 1 ml lysis buffer (1% NP40/20 mM HEPES, pH 7.5/5 mM $MgCl_2$/1 mM DTT/10 mg/ml aprotinen/2 mg/ml leupeptin/2 mg/ml antipain/0.5 mM PMSF) and the lysates cleared by centrifugation at 100,000×g for 45 min. Alternatively, four hours after the addition of the labelling media, the media is removed, the cells washed, and 3 ml of media containing the same or a different test compound added. Following an additional 16 hour incubation, the lysis is carried out as above. Aliquots of lysates containing equal numbers of acid-precipitable counts are bought to 1 ml with IP buffer (lysis buffer lacking DTT) and immunoprecipitated with the ras-specific monoclonal antibody Y13-259 (Furth, M. E. et al., J. Virol. 43:294–304, (1982)). Following a 2 hour antibody incubation at 4° C., 200 ml of a 25% suspension of protein A-Sepharose coated with rabbit anti rat IgG is added for 45 min. The immunoprecipitates are washed four times with IP buffer (20 nM HEPES, pH 7.5/1 mM EDTA/1% Triton X-100.0.5% deoxycholate/0.1%/SDS/0.1 M NaCl) boiled in SDS-PAGE sample buffer and loaded on 13% acrylamide gels. When the dye front reached the bottom, the gel is fixed, soaked in Enlightening, dried and autoradiographed. The intensities of the bands corresponding to prenylated and nonprenylated Ras proteins are compared to determine the percent inhibition of prenyl transfer to protein.

Example 8

Cell-based in Vitro Anchorage Independent Growth Assay (SALSA)

SALSA (Soft Agar-Like Surrogate Assay) measures the inhibition of anchorage-independent growth by prenyl-transferase inhibitors. Only transformed cells are able to grow anchorage-independently in the SALSA format. Additionally, cells growing in the SALSA format grow in clumps, resembling the colonies formed in soft agar. SALSA may been used to measure the growth inhibition by prenyl-transferase inhibitors in a variety of transformed cell lines, including Rat1 fibroblasts transformed with viral-H-ras (H-ras/rat1), as well as a panel of human tumor cell lines (HTL's).

SALSA is performed in 96-well plates that are coated with a thin film of the polymer, PolyHEMA (Poly(2-hydroxyethyl methacrylate)), which prevents cells from attaching to the plate. Rat1 fibroblast cells transformed with v-Ha-ras (this cell line has been deposited in the ATCC on Aug. 19, 1997 under the terms of the Budapest convention and has been given a designation of ATCC 12387) are seeded at 5000 cells/well, grown for 4 hr, then vehicle or half-log dilutions of test compound (in either an 8 or 12 point titration) are added. The cells are then grown for 6 days at 37 degrees, without changing the growth media or adding fresh compound. At day 6, cell growth is assessed via a calorimetric assay that measures the cleavage of the tetrazolium dye, MTT, to an insoluble purple formazan, a reaction dependent upon mitochondrial dehydrogenases. At day 6, the cells are incubated for 4 hr with 0.5 mg/ml MTT, and then SDS is added to 9% w/v to lyse the cells and solubilize the insoluble MTT-formazan. The amount of MTT metabolism is quantitated via spectrophotometric detection at 570 nM. Dose-inhibition curves and $IC_{50}$'s are determined.

Example 9

Construction of SEAP Reporter Plasmid pDSE100

The SEAP reporter plasmid, pDSE100 was constructed by ligating a restriction fragment containing the SEAP coding sequence into the plasmid pCMV-RE-AKI. The SEAP gene is derived from the plasmid pSEAP2-Basic (Clontech, Palo Alto, Calif.). The plasmid pCMV-RE-AKI was constructed by Deborah Jones (Merck) and contains 5 sequential copies of the 'dyad symmetry response element' cloned upstream of a 'CAT-TATA' sequence derived from the cytomegalovirus immediate early promoter. The plasmid also contains a bovine growth hormone poly-A sequence.

The plasmid, pDSE100 was constructed as follows. A restriction fragment encoding the SEAP coding sequence was cut out of the plasmid pSEAP2-Basic using the restriction enzymes EcoR1 and HpaI. The ends of the linear DNA fragments were filled in with the Klenow fragment of *E. coli* DNA Polymerase I. The 'blunt ended' DNA containing the SEAP gene was isolated by electrophoresing the digest in an agarose gel and cutting out the 1694 base pair fragment. The vector plasmid pCMV-RE-AKI was linearized with the restriction enzyme Bgl-II and the ends filled in with Klenow DNA Polymerase I. The SEAP DNA fragment was blunt end ligated into the pCMV-RE-AKI vector and the ligation products were transformed into DH5-alpha *E. coli* cells (Gibco-BRL). Transformants were screened for the proper insert and then mapped for restriction fragment orientation. Properly oriented recombinant constructs were sequenced across the cloning junctions to verify the correct sequence. The resulting plasmid contains the SEAP coding sequence downstream of the DSE and CAT-TATA promoter elements and upstream of the BGH poly-A sequence.

Cloning of a Myristylated Viral-H-ras Expression Plasmid

A DNA fragment containing viral-H-ras can be PCRed from plasmid "H-1" (Ellis R. et al. J. Virol. 36, 408, 1980) using the following oligos.

```
Sense strand:                              (SEQ.ID.NO.: 14)
5'TCTCCTCGAGGCCACCATGGGGAGTAGCAAGAGCAAGCCTAA
GGACCCCAGCCAGCGCCGGATGACAGAATACAAGCTTGTGGTG
G 3'.

Antisense:                                 (SEQ.ID.NO.: 15)
5'CACATCTAGATCAGGACAGCACAGACTTGCAGC 3'.
```

A sequence encoding the first 15 aminoacids of the v-src gene, containing a myristylation site, is incorporated into the sense strand oligo. The sense strand oligo also optimizes the 'Kozak' translation initiation sequence immediately 5' to the ATG start site. To prevent prenylation at the viral-ras C-terminus, cysteine 186 would be mutated to a serine by substituting a G residue for a C residue in the C-terminal antisense oligo. The PCR primer oligos introduce an XhoI site at the 5' end and a XbaI site at the 3' end. The XhoI-XbaI fragment can be ligated into the mammalian expression plasmid pCI (Promega) cut with XhoI and XbaI. This results in a plasmid in which the recombinant myr-viral-H-ras gene is constitutively transcribed from the CMV promoter of the pCI vector.

Cloning of a Viral-H-ras-CVLL Expression Plasmid

A viral-H-ras clone with a C-terminal sequence encoding the amino acids CVLL can be cloned from the plasmid "H-1" (Ellis R. et al. J. Virol. 36, 408, 1980) by PCR using the following oligos.

```
Sense strand:                              (SEQ.ID.NO.: 16)
5'TCTCCTCGAGGCCACCATGACAGAATACAAGCTTGTGGTGG-3'

Antisense strand:                          (SEQ.ID.NO.: 17)
5'CACTCTAGACTGGTGTCAGAGCAGCACACACTTGCAGC-3'
```

The sense strand oligo optimizes the 'Kozak' sequence and adds an XhoI site. The antisense strand mutates serine 189 to leucine and adds an XbaI site. The PCR fragment can be trimmed with XhoI and XbaI and ligated into the XhoI-XbaI cut vector pCI (Promega). This results in a plasmid in which the mutated viral-H-ras-CVLL gene is constitutively transcribed from the CMV promoter of the pCI vector.

Cloning of c-H-ras-Leu61 Expression Plasmid

The human c-H-ras gene can be PCRed from a human cerebral cortex cDNA library (Clontech) using the following oligonucleotide primers.

```
Sense strand:                              (SEQ.ID.NO.: 18)
5'-GAGAGAATTCGCCACCATGACGGAATATAAGCTGGTGG-3'

Antisense strand:                          (SEQ.ID.NO.: 19)
5'-GAGAGTCGACGCGTCAGGAGAGCACACACTTGC-3'
```

The primers will amplify a c-H-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-H-ras fragment can be ligated ligated into an EcoRI-Sal I cut mutagenesis vector pAlter-1 (Promega). Mutation of glutamine-61 to a leucine can be accomplished using the manufacturer's protocols and the following oligonucleotide:

```
5'-CCGCCGGCCTGGAGGAGTACAG-3'       (SEQ.ID.NO.: 20)
```

After selection and sequencing for the correct nucleotide substitution, the mutated c-H-ras-Leu61 can be excised from the pAlter-1 vector, using EcoRI and Sal I, and be directly ligated into the vector pCI (Promega) which has been digested with EcoRI and Sal I. The new recombinant plasmid will constitutively transcribe c-H-ras-Leu61 from the CMV promoter of the pCI vector.

Cloning of a c-N-ras-Val-12 Expression Plasmid

The human c-N-ras gene can be PCRed from a human cerebral cortex cDNA library (Clontech) using the following oligonucleotide primers.

```
Sense strand:                              (SEQ.ID.NO.: 21)
5'-GAGAGAATTCGCCACCATGACTGAGTACAAACTGGTGG-3'

Antisense strand:                          (SEQ.ID.NO.: 22)
5'-GAGAGTCGACTTGTTACATCACCACACATGGC-3'
```

The primers will amplify a c-N-ras encoding DNA fragment with the primers contributing an optimized 'Kozak' translation start sequence, an EcoRI site at the N-terminus and a Sal I stite at the C-terminal end. After trimming the ends of the PCR product with EcoRI and Sal I, the c-N-ras fragment can be ligated into an EcoRI —Sal I cut mutagenesis vector pAlter-1 (Promega). Mutation of glycine-12 to a valine can be accomplished using the manufacturer's protocols and the following oligonucleotide:

```
5'-GTTGGAGCAGTTGGTGTTGGG-3'        (SEQ.ID.NO.: 23)
```

After selection and sequencing for the correct nucleotide substitution, the mutated c-N-ras-Val-12 can be excised from the pAlter-1 vector, using EcoRI and Sal I, and be directly ligated into the vector pCI (Promega) which has been digested with EcoRI and Sal I. The new recombinant plasmid will constitutively transcribe c-N-ras-Val-12 from the CMV promoter of the pCI vector.

Cloning of a c-K-ras-Val-12 Expression Plasmid

The human c-K-ras gene can be PCRed from a human cerebral cortex cDNA library (Clontech) using the following oligonucleotide primers.

```
Sense strand:                              (SEQ.ID.NO.: 24)
5'-GAGAGGTACCGCCACCATGACTGAATATAAACTTGTGG-3'

Antisense strand:                          (SEQ.ID.NO.: 25)
5'-CTCTGTCGACGTATTTACATAATTACACACTTTGTC-3'
```

The primers will amplify a c-K-ras encoding DNA fragment with the primers contributing an optimized 'Kozak' translation start sequence, a KpnI site at the N-terminus and a Sal I stite at the C-terminal end. After trimming the ends of the PCR product with Kpn I and Sal I, the c-K-ras fragment can be ligated into a KpnI-Sal I cut mutagenesis vector pAlter-1 (Promega). Mutation of cysteine-12 to a valine can be accomplished using the manufacturer's protocols and the following oligonucleotide:

```
5'-GTAGTTGGAGCTGTTGGCGTAGGC-3'     (SEQ.ID.NO.: 26)
```

After selection and sequencing for the correct nucleotide substitution, the mutated c-K-ras-Val-12 can be excised from the pAlter-1 vector, using KpnI and Sal I, and be directly ligated into the vector pCI (Promega) which has been digested with KpnI and Sal I. The new recombinant plasmid will constitutively transcribe c-K-ras-Val-12 from the CMV promoter of the pCI vector.

SEAP Assay

Human $C_{33}A$ cells (human epitheial carcenoma—ATTC collection) are seeded in 10 cm tissue culture plates in DMEM+10% fetal calf serum+1×Pen/Strep+1×glutamine+1×NEAA. Cells are grown at 37° C. in a 5% $CO_2$ atmosphere until they reach 50–80% of conflunecy.

The transient transfection is performed by the $CaPO_4$ method (Sambrook et al., 1989). Thus, expression plasmids for H-ras, N-ras, K-ras, Myr-ras or H-ras-CVLL are co-precipitated with the DSE-SEAP reporter construct. For 10 cm plates 600 ml of $CaCl_2$-DNA solution is added dropwise while vortexing to 600 ml of 2×HBS buffer to give 1.2 ml of precipitate solution (see recipes below). This is allowed to sit at room temperature for 20 to 30 minutes. While the precipitate is forming, the media on the $C_{33}A$ cells is replaced with DMEM (minus phenol red; Gibco cat. #31053-028)+0.5% charcoal stripped calf serum+1×(Pen/Strep, Glutamine and nonessential aminoacids). The $CaPO_4$-DNA precipitate is added dropwise to the cells and the plate rocked gently to distribute. DNA uptake is allowed to proceed for 5–6 hrs at 37° C. under a 5% $CO_2$ atmosphere.

Following the DNA incubation period, the cells are washed with PBS and trypsinized with 1 ml of 0.05% trypsin. The 1 ml of trypsinized cells is diluted into 10 ml of phenol red free DMEM+0.2% charcoal stripped calf serum +1×(Pen/Strep, Glutamine and NEAA). Transfected cells are plated in a 96 well microtiter plate (100 ml/well) to which drug, diluted in media, has already been added in a volume of 100 ml. The final volume per well is 200 ml with each drug concentration repeated in triplicate over a range of half-log steps.

Incubation of cells and drugs is for 36 hrs at 37° under $CO_2$. At the end of the incubation period, cells are examined microscopically for evidence of cell distress. Next, 100 ml of media containing the secreted alkaline phosphatase is removed from each well and transferred to a microtube array for heat treatment at 65° C. for 1 hr to inactivate endogenous alkaline phosphatases (but not the heat stable secreted phosphatase).

The heat treated media is assayed for alkaline phosphatase by a luminescence assay using the luminescence reagent CSPD® (Tropix, Bedford, Mass.). A volume of 50 ml media is combinRased with 200 ml of CSPD cocktail and incubated for 60 minutes at room temperature. Luminesence is monitored using an ML2200 microplate luminometer (Dynatech). Luminescence reflects the level of activation of the fos reporter construct stimulated by the transiently expressed protein.

| DNA-$CaPO_4$ precipitate for 10 cm, plate of cells | |
|---|---|
| Ras expression plasmid (1 mg/ml) | 10 ml |
| DSE-SEAP Plasmid (1 mg/ml) | 2 ml |
| Sheared Calf Thymus DNA (1 mg/ml) | 8 ml |
| 2M $CaCl_2$ | 74 ml |
| $dH_2O$ | 506 ml |

2X HBS Buffer

| | |
|---|---|
| 280 mM | NaCl |
| 10 mM | KCl |
| 1.5 mM | $Na_2HPO_42H_2O$ |
| 12 mM | dextrose |
| 50 mM | HEPES |
| | Final pH = 7.05 |

Luminesence Buffer (26 ml)

| | |
|---|---|
| Assay Buffer | 20 ml |
| Emerald Reagent ™ (Tropix) | 2.5 ml |
| 100 mM homoarginine | 2.5 ml |
| CSPD Reagent ® (Tropix) | 1.0 ml |

Assay Buffer

Add 0.05M $Na_2CO_3$ to 0.05M $NaHCO_3$ to obtain pH 9.5. Make 1 mM in $MgCl_2$

Example 10

In Vivo Tumor Growth Inhibition Assay (nude mouse)

In vivo efficacy as an inhibitor of the growth of cancer cells may be confirmed by several protocols well known in the art. Examples of such in vivo efficacy studies are described by N. E. Kohl et al. (*Nature Medicine*, 1:792–797 (1995)) and N. E. Kohl et al. (*Proc. Nat. Acad. Sci. U.S.A.*, 91:9141–9145 (1994)).

Rodent fibroblasts transformed with oncogenically mutated human Ha-ras or Ki-ras ($10^6$ cells/animal in 1 ml of DMEM salts) are injected subcutaneously into the left flank of 8–12 week old female nude mice (Harlan) on day 0. The mice in each oncogene group are randomly assigned to a vehicle, compound or combination treatment group. Animals are dosed subcutaneously starting on day 1 and daily for the duration of the experiment. Alternatively, the farnesyl-protein transferase inhibitor may be administered by a continuous infusion pump. Compound, compound combination or vehicle is delivered in a total volume of 0.1 ml. Tumors are excised and weighed when all of the vehicle-treated animals exhibited lesions of 0.5–1.0 cm in diameter, typically 11–15 days after the cells were injected. The average weight of the tumors in each treatment group for each cell line is calculated.

What is claimed is:

1. A compound which inhibits farnesyl-protein transferase of the formula A:

A

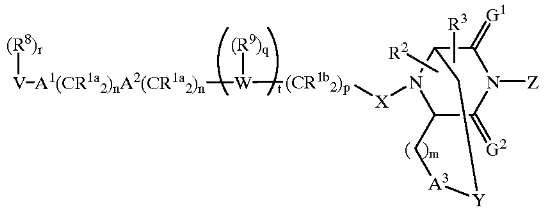

wherein:

$R^{1a}$ and $R^{1b}$ are independently selected from:

a) hydrogen, b) aryl, heterocycle, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $CN(R^{10})_2NC(O)$—, $(R^{10})_2N$—$C(NR^{10})$—, CN, $NO_2$, $R^{10}C(O)$—, $N_3$, —$N(R^{10})_2$, or $R^{11}OC(O)NR^{10}$—, c) unsubstituted or substituted $C_1$–$C_6$ alkyl wherein the substitutent on the substituted $C_1$–$C_6$ alkyl is selected from unsubstituted or substituted aryl, heterocyclic, $C_3$–$C_{10}$ cycloalkyl, $C_2$–$C_6$ alkenyl, $C_2$–$C_6$ alkynyl, $R^{10}O$—, $R^{11}S(O)_m$—, $R^{10}C(O)NR^{10}$—, $(R^{10})_2NC(O)$—, CN, $(R^{10})_2N$—$C(NR^{10})$—, $R^{10}C(O)$—, $N_3$, —$N(R^{10})_2$, and $R^{11}OC(O)$—$NR^{10}$—;

$R^2$ and $R^3$ are independently selected from: H, unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

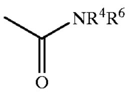 or 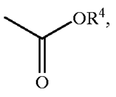

wherein the substituted group is substituted with one or more of:

1) aryl or heterocycle, unsubstituted or substituted with:

a) $C_{1-4}$ alkyl, b) $(CH_2)_pOR^4$, c) $(CH_2)_pNR^4R^6$, d) halogen, e) CN,

2) $C_{3-6}$ cycloalkyl,

3) $OR^4$,

4) $SR^5$, $S(O)R^5$, $SO_2R^5$,

5) —$NR^4R^6$,

6)

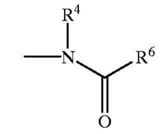

7)

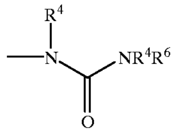

8)

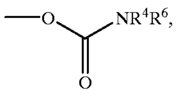

9)

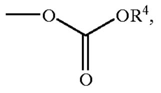

10)

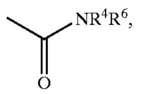

11)

—$SO_2$—$NR^4R^6$,

-continued

12) 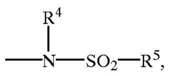

13) 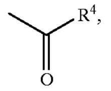

14) 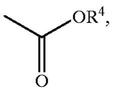

15) $N_3$, or

16) F;

or $R^2$ and $R^3$ are attached to the same C atom and are combined to form —$(CH_2)_u$— wherein one of the carbon atoms is optionally replaced by a moiety selected from: O, $S(O)_m$, —NC(O)—, and —$N(COR^{10})$—;

and $R^2$ and $R^3$ are optionally attached to the same carbon atom;

$R^4$ and $R^6$ are independently selected from: H, $C_{1-4}$ alkyl, $C_{3-6}$ cycloalkyl, heterocycle, aryl, aroyl, heteroaroyl, arylsulfonyl, heteroarylsulfonyl, unsubstituted or substituted with:

a) $C_{1-4}$ alkoxy, b) aryl or heterocycle, c) halogen, d) HO, e) 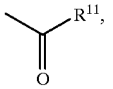

f) —$SO_2R^{11}$, or g) $N(R^{10})_2$; or $R^4$ and $R^6$ may be joined in a ring;

$R^5$ is selected from: $C_{1-4}$ alkyl, $C_{3-6}$ cycloalkyl, heterocycle, aryl, unsubstituted or substituted with:

a) $C_{1-4}$ alkoxy, b) aryl or heterocycle, c) halogen, d) HO e) 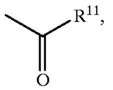

f) —$SO_2R^{11}$, or g) $N(R^{10})_2$;

$R^8$ is independently selected from:

a) hydrogen, b) aryl, heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^{10}O$—, $R^{11}$ $S(O)_m$—, $R^{10}C(O)NR^{10}$—, $(R^{10})_2NC(O)$—, $(R10)_2N$—$C(NR^{10})$—, CN, $NO_2$, $R^{10}C(O)$—, $N_3$, —$N(R^{10})_2$, or $R^{11}OC(O)NR^{10}$—, and c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^{10}O$—, $R^{11}$ $S(O)_m$—, $R^{10}C(O)NH$—, $(R^{10})_2NC(O)$—, $R^{10}{}_2N$—$C(NR^{10})$—, CN, $R^{10}C(O)$—, $N_3$, —$N(R^{10})_2$, or $R^{10}OC(O)NH$—;

$R^9$ is selected from:

a) hydrogen, b) alkenyl, alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, and c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, or $R^{11}OC(O)NR^{10}$—;

$R^{10}$ is independently selected from hydrogen, $C_1$–$C_{14}$ alkyl, unsubstituted or substituted benzyl and unsubstituted or substituted aryl;

$R^{11}$ is independently selected from $C_1$–$C_6$ alkyl and unsubstituted or substituted aryl;

$A^1$ and $A^2$ are independently selected from: a bond, —CH=CH—, —C≡C—, —C(O)—, —$C(O)NR^{10}$—, —$NR^{10}C(O)$—, O, —$N(R^{10})$—, —$S(O)_2N(R^{10})$—, —$N(R^{10})S(O)_2$—, or $S(O)_m$;

$A^3$ is selected from:

a) a bond, b) unsubstituted or substituted aryl, and c) unsubstituted or substituted heteroaryl;

$G^1$ and $G^2$ are independently selected from: O or $H_2$;

V is selected from:

a) hydrogen, b) heterocycle, c) aryl, d) $C_1$–$C_{20}$ alkyl wherein from 0 to 4 carbon atoms are replaced with a heteroatom selected from O, S, and N, and e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

X is selected from a bond, —$CH_2$—, —C(=O)—, or —$S(=O)_m$;

Y is selected from: a bond, —CH=CH—, —C(O)—, —$C(O)NR^{10}$—, —$NR^{10}C(O)$—, O, —$N(R^{10})$—, —$S(O)_2N(R^{10})$—, —$N(R^{10})S(O)_2$—, or $S(O)_m$;

Z is selected from:

1) an unsubstituted or substituted group selected from aryl, heteroaryl, arylmethyl, heteroarylmethyl, arylsulfonyl, and heteroarylsulfonyl, wherein the substituted group is substituted with one or more of:

a) $C_{1-4}$ alkyl, unsubstituted or substituted with: $C_{1-4}$ alkoxy, $NR^4R^6$, $C_{3-6}$ cycloalkyl, unsubstituted or substituted aryl, heterocycle, HO, —$S(O)_mR^5$, or —$C(O)NR^4R^6$, b) aryl or heterocycle, c) halogen, d) $OR^4$, e) $NR^4R^6$, f) CN, g) $NO_2$, h) $CF_3$, i) —$S(O)_mR^5$, j) $-C(O)NR^4R^6$, or k) $C_3-C_6$ cycloalkyl; or 2) an unsubstituted or substituted group selected from the group consisting of $C_1-C_6$ alkyl and $C_3-C_6$ cycloalkyl, wherein the substituted group is substituted with one or two of the following:

a) $C_{1-4}$ alkoxy, b) $NR^4R^6$, c) $C_{3-6}$ cycloalkyl d) $-NR^4C(O)R^6$, e) HO, f) $-S(O)_mR^5$, g) halogen, or h) perfluoroalkyl;

m is 0, 1 or 2;

n is 0, 1, 2, 3 or 4;

p is 0, 1, 2, 3 or 4;

q is 1 or 2;

r is 0, 1, 2, 3, 4 or 5; provided that r is 0 when V is hydrogen;

t is 0 or 1; and u is 4 or 5;

or the pharmaceutically acceptable salts thereof.

2. A compound which inhibits farnesyl-protein transferase of the formula B:

B

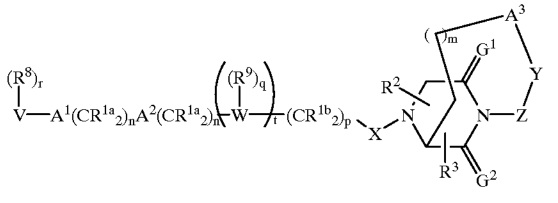

wherein:

$R^{1a}$ and $R^{1b}$ are independently selected from:

a) hydrogen, b) aryl, heterocycle, $C_3-C_{10}$ cycloalkyl, $C_2-C_6$ alkenyl, $C_2-C_6$ alkynyl, $R^{10}O-$, $R^{11}S(O)_m-$, $R^{10}C(O)NR^{10}-$, $CN(R^{10})_2NC(O)-$, $(R^{10})_2N-C(NR^{10})-$, CN, $NO_2$, $R^{10}C(O)-$, $N_3$, $-N(R^{10})_2$, or $R^{11}OC(O)NR^{10}-$, c) unsubstituted or substituted $C_1-C_6$ alkyl wherein the substitutent on the substituted $C_1-C_6$ alkyl is selected from unsubstituted or substituted aryl, heterocyclic, $C_3-C_{10}$ cycloalkyl, $C_2-C_6$ alkenyl, $C_2-C_6$ alkynyl, $R^{10}O-$, $R^{11}S(O)_m-$, $R^{10}C(O)NR^{10}-$, $(R^{10})_2NC(O)-$, CN, $(R^{10})_2N-C(NR^{10})-$, $R^{10}C(O)-$, $N_3$, $-N(R^{10})_2$, and $R^{11}OC(O)-NR^{10}-$;

$R^2$ and $R^3$ are independently selected from: H, unsubstituted or substituted $C_{1-8}$ alkyl, unsubstituted or substituted $C_{2-8}$ alkenyl, unsubstituted or substituted $C_{2-8}$ alkynyl, unsubstituted or substituted aryl, unsubstituted or substituted heterocycle,

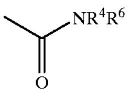 or 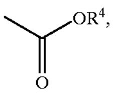

wherein the substituted group is substituted with one or more of:

1) aryl or heterocycle, unsubstituted or substituted with:

a) $C_{1-4}$ alkyl, b) $(CH_2)_pOR^4$, c) $(CH_2)_pNR^4R^6$, d) halogen, e) CN,

2) $C_{3-6}$ cycloalkyl,

3) $OR^4$,

4) $SR^5$, $S(O)R^5$, $SO_2R^5$,

5) $-NR^4R^6$,

6)

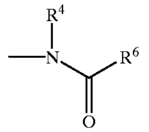

7)

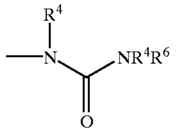

8)

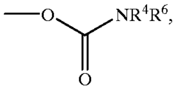

9)

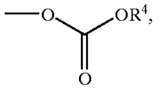

10)

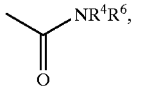

11) $-SO_2-NR^4R^6$,

12)

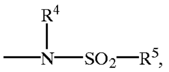

13)

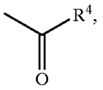

14)

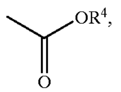

15) $N_3$, or

16) F;

or $R^2$ and $R^3$ are attached to the same C atom and are combined to form $-(CH_2)_u-$ wherein one of the carbon atoms is optionally replaced by a moiety selected from: O, $S(O)_m$, $-NC(O)-$, and $-N(COR^{10})-$;

and $R^2$ and $R^3$ are optionally attached to the same carbon atom;

$R^4$ and $R^6$ are independently selected from: H, $C_{1-4}$ alkyl, $C_{3-6}$ cycloalkyl, heterocycle, aryl, aroyl, heteroaroyl, arylsulfonyl, heteroarylsulfonyl, unsubstituted or substituted with:

a) $C_{1-4}$ alkoxy,
b) aryl or heterocycle,
c) halogen,
d) HO
e)

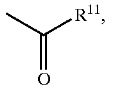

f) —$SO_2R^{11}$, or
g) $N(R^{10})_2$; or $R^4$ and $R^6$ may be joined in a ring;

$R^5$ is selected from: $C_{1-4}$ alkyl, $C_{3-6}$ cycloalkyl, heterocycle, aryl, unsubstituted or substituted with:

a) $C_{1-4}$ alkoxy,
b) aryl or heterocycle,
c) halogen,
d) HO,
e)

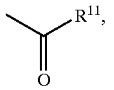

f) —$SO_2R^{11}$, or
g) $N(R^{10})_2$;

$R^8$ is independently selected from:

a) hydrogen,
b) aryl, heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^{10}O$—, $R^{11}S(O)_m$—, $R^{10}OC(O)NR^{10}$—, $(R^{10})_2NC(O)$—, $(R10)_2N$—$C(NR^{10})$—, CN, $NO_2$, $R^{10}C(O)$—, $N_3$, —$N(R^{10})_2$, or $R^{11}OC(O)NR^{10}$—, and
c) $C_1$–$C_6$ alkyl unsubstituted or substituted by aryl, cyanophenyl, heterocycle, $C_3$–$C_{10}$ cycloalkyl, $C_2$–$C_6$ alkenyl, $C_2$–$C_6$ alkynyl, $C_1$–$C_6$ perfluoroalkyl, F, Cl, Br, $R^{10}O$—, $R^{11}S(O)_m$—, $R^{10}C(O)NH$—, $(R^{10})_2NC(O)$—, $R^{10}{}_2N$—$C(NR^{10})$—, CN, $R^{10}C(O)$—, $N_3$, —$N(R^{10})_2$, or $R^{10}OC(O)NH$—;

$R^9$ is selected from:

a) hydrogen,
b) alkenyl, alkynyl, perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $NO_2$, $R^{10}C(O)$—, $N_3$, —$N(R^{10})_2$, or $R^{11}OC(O)NR^{10}$—, and
c) $C_1$–$C_6$ alkyl unsubstituted or substituted by perfluoroalkyl, F, Cl, Br, $R^{10}O$—, $R^{11}S(O)_m$—, $R^{10}C(O)NR^{10}$—, $(R^{10})_2NC(O)$—, $R^{10}{}_2N$—$C(NR^{10})$—, CN, $R^{10}C(O)$—, $N_3$, —$N(R^{10})_2$, or $R^{11}OC(O)NR^{10}$—;

$R^{10}$ is independently selected from hydrogen, $C_1$—$C_{14}$ alkyl, unsubstituted or substituted benzyl and unsubstituted or substituted aryl;

$R^{11}$ is independently selected from $C_1$–$C_6$ alkyl and unsubstituted or substituted aryl;

$A^1$ and $A^2$ are independently selected from: a bond, —CH═CH—, —C≡C—, —C(O)—, —$C(O)NR^{10}$—, —$NR^{10}C(O)$—, O, —$N(R^{10})$—, —$S(O)_2N(R^{10})$—, —$N(R^{10})S(O)_2$—, or $S(O)_m$;

$A^3$ is selected from:

a) a bond,
b) unsubstituted or substituted aryl, or
c) unsubstituted or substituted heteroaryl;

$G^1$ and $G^2$ are independently sele(:ted from: O or $H_2$;

V is selected from:

a) hydrogen,
b) heterocycle,
c) aryl,
d) $C_1$–$C_{20}$ alkyl wherein from 0 to 4 carbon atoms are replaced with a heteroatom selected from O, S, and N, and
e) $C_2$–$C_{20}$ alkenyl, provided that V is not hydrogen if $A^1$ is $S(O)_m$ and V is not hydrogen if $A^1$ is a bond, n is 0 and $A^2$ is $S(O)_m$;

W is a heterocycle;

X is selected from a bond, —$CH_2$—, —C(═O)—, or —$S(=O)_m$;

Y is selected from: a bond, —CH═CH—, —C(O)—, —$C(O)NR^{10}$—, —$NR^{10}C(O)$—, O, —$N(R^{10})$—, —$S(O)_2N(R^{10})$—, —$N(R^{10})S(O)_2$—, or $S(O)_m$;

Z is selected from:

1) an unsubstituted or substituted group selected from aryl, heteroaryl, arylmethyl, heteroarylmethyl, arylsulfonyl, heteroarylsulfonyl, wherein the substituted group is substituted with one or more of:
   a) $C_{1-4}$ alkyl, unsubstituted or substituted with: $C_{1-4}$ alkoxy, $NR^4R^6$, $C_{3-6}$ cycloalkyl, unsubstituted or substituted aryl, heterocycle, HO, —$S(O)_mR^5$, or —$C(O)NR^4R^6$,
   b) aryl or heterocycle,
   c) halogen,
   d) $OR^4$,
   e) $NR^4R^6$,
   f) CN,
   g) $NO_2$,
   h) $CF_3$,
   i) —$S(O)_mR^5$,
   j) —$C(O)NR^4R^6$, or
   k) $C_3$–$C_6$ cycloalkyl; or
2) an unsubstituted or substituted group selected from $C_1$–$C_6$ alkyl or $C_3$–$C_6$ cycloalkyl, wherein the substituted group is substituted with one or two of the following:
   a) $C_{1-4}$ alkoxy,
   b) $NR^4R^6$,
   c) $C_{3-6}$ cycloalkyl
   d) —$NR^4C(O)R^6$,
   e) HO,
   f) —$S(O)_mR^5$,
   g) halogen, or
   h) perfluoroalkyl;

m is 0, 1 or 2;

n is 0, 1, 2, 3 or 4;

p is 0, 1, 2, 3 or 4;

q is 1 or 2;

r is 0, 1, 2, 3, 4, or 5; provided that r is 0 when V is hydrogen;

t is 0 or 1; and u is 4 or 5;

or the pharmaceutically acceptable salts thereof.

3. The compound according to claim 1 of Formula C:

C

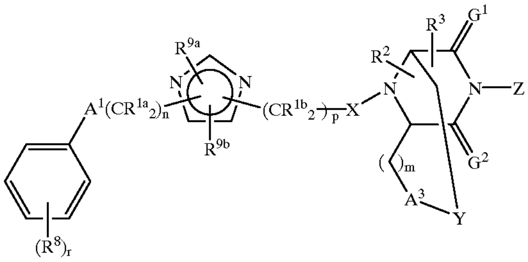

wherein:

$R^{1a}$ is selected from: hydrogen, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^{10}O$—, —$N(R^{10})_2$, or $C_2$–$C_6$ alkenyl, and c) C 1–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^3$ is selected from H and $CH_3$;

$R^2$ is selected from: H;

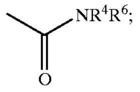

or $C_{1-5}$ alkyl, unbranched or branched, unsubstituted or substituted with one or more of:

1) aryl, 2) heterocycle,

3) $OR^4$,

4) $SR^5$, $SO_2R^5$, or

5)

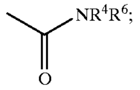

and $R^2$ and $R^3$ are optionally attached to the same carbon atom;

$R^4$ and $R^6$ are independently selected from:

H, $C_{1-4}$ alkyl, $C_{3-6}$ cycloalkyl, aryl, heterocycle, unsubstituted or substituted with:

a) $C_{1-4}$ alkoxy, b) halogen, or c) aryl or heterocycle;

$R^5$ is selected from:

$C_{1-4}$ alkyl or $C_{3-6}$ cycloalkyl, unsubstituted or substituted with:

a) $C_{1-4}$ alkoxy, b) halogen, or c) aryl or heterocycle;

$R^8$ is independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{9a}$ and $R^{9b}$ are independently selected from hydrogen, ethyl, cyclopropyl or methyl;

$R^{10}$ is independently selected from hydrogen, $C_1$–$C_{14}$ alkyl, substituted or unsubstituted benzyl and substituted or unsubstituted aryl;

$R^{11}$ is independently selected from $C_1$–$C_6$ alkyl and substituted or unsubstituted aryl;

$A^1$ is selected from: a bond, —C(O)—, O, —$N(R^{10})$—, or $S(O)_m$;

$A^3$ is selected from:

a) a bond, b) unsubstituted or substituted aryl, and c) unsubstituted or substituted heteroaryl;

$G^1$ and $G^2$ are independently selected from: O or $H_2$;

X is selected from a bond, —$CH_2$—, —C(=O)—, or —$S(=O)_m$;

Y is selected from: a bond O;

Z is an unsubstituted or substituted aryl, wherein the substituted aryl is substituted with one or more of the following:

a) $C_{1-4}$ alkyl, unsubstituted or substituted with:

1) $C_{1-4}$ alkoxy,

2) $NR^4R^6$,

3) $C_{3-6}$ cycloalkyl, 4) unsubstituted or substituted aryl, 5) heterocycle,

6) HO,

7) —$S(O)_mR^5$, or

8) —$C(O)NR^4R^6$, b) aryl or heterocycle, c) halogen, d) $OR^4$, e) $NR^4R^6$, f) CN, g) $NO_2$, h) $CF_3$, i) —$S(O)_mR^5$, j) —$C(O)NR^4R^6$, or k) $C_3$–$C_6$ cycloalkyl;

m is 0, 1 or 2;

n is 0 or 1; provided that n is not 0 if $A^1$ is a bond, O, —$N(R^{10})$— or $S(O)_m$;

p is 0, 1, 2, 3 or 4; and r is 0, 1, 2, 3, 4, or 5;

or the pharmaceutically acceptable salts thereof.

4. The compound according to claim 2 of Formula D

D

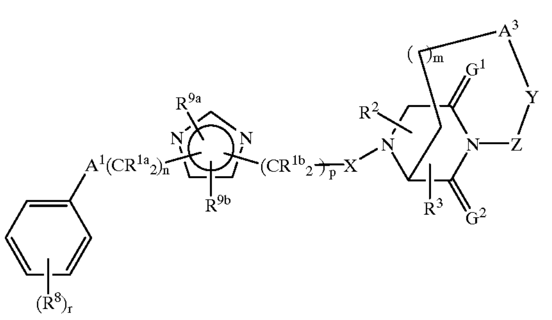

wherein:

$R^{1a}$ is selected from: hydrogen, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^{10}O$—, —$N(R^{10})_2$, or $C_2$–$C_6$ alkenyl, and c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^3$ is selected from H and $CH_3$;

$R^2$ is selected from: H;

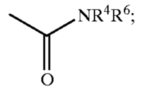

for $C_{1-5}$ alkyl, unbranched or branched, unsubstituted or substituted with one or more of:

1) aryl, 2) heterocycle,

3) $OR^4$,

4) $SR^5$, $SO_2R^5$, or

5)

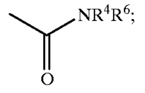

and $R^2$ and $R^3$ are optionally attached to the same carbon atom;

$R^4$ and $R^6$ are independently selected from:

H, $C_{1-4}$ alkyl, $C_{3-6}$ cycloalkyl, aryl, heterocycle, unsubstituted or substituted with:

a) $C_{1-4}$ alkoxy, b) halogen, or c) aryl or heterocycle;

$R^5$ is selected from:

$C_{1-4}$ alkyl or $C_{3-6}$ cycloalkyl, unsubstituted or substituted with:

a) $C_{1-4}$ alkoxy, b) halogen, or c) aryl or heterocycle;

$R^8$ is independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{9a}$ and $R^{9b}$ are independently selected from hydrogen, ethyl, cyclopropyl or methyl;

$R^{10}$ is independently selected from hydrogen, $C_1$–$C_{14}$ alkyl, substituted or unsubstituted benzyl and substituted or unsubstituted aryl;

$R^{11}$ is independently selected from $C_1$–$C_6$ alkyl and substituted or unsubstituted aryl;

$A^1$ is selected from: a bond, —C(O)—, O, —$N(R^{10})$—, or $S(O)_m$;

$A^3$ is selected from:

a) a bond, b) unsubstituted or substituted aryl, and c) unsubstituted or substituted heteroaryl;

$G^1$ and $G^2$ are independently selected from: O or $H_2$;

X is selected from a bond, —$CH_2$—, —C(=O)—, or —$S(=O)_m$;

Y is selected from: a bond O;

Z is an unsubstituted or substituted aryl, wherein the substituted aryl is substituted with one or more of the following:

a) $C_{1-4}$ alkyl, unsubstituted or substituted with:

1) $C_{1-4}$ alkoxy,

2) $NR^4R^6$,

3) $C_{3-6}$ cycloalkyl, 4) unsubstituted or substituted aryl, 5) heterocycle,

6) HO,

7) —$S(O)_mR^5$, or

8) —$C(O)NR^4R^6$, b) aryl or heterocycle, c) halogen, d) $OR^4$, e) $NR^4R^6$, f) CN, g) $NO_2$, h) $CF_3$, i) —$S(O)_mR^5$, j) —$C(O)NR^4R^6$, or k) $C_3$–$C_6$ cycloalkyl;

m is 0, 1 or 2;

n is 0 or 1; provided that n is not 0 if $A^1$ is a bond, O, —$N(R^{10})$— or $S(O)_m$;

p is 0, 1, 2, 3 or 4; and r is 0, 1, 2, 3, 4 or 5;

or the pharmaceutically acceptable salts thereof.

5. The compound according to claim 3 of Formula E:

E

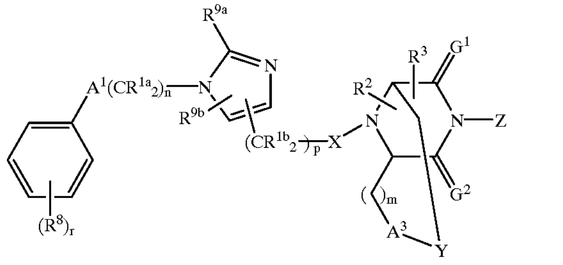

wherein:

$R^{1a}$ is selected from: hydrogen, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^{10}O$—, —$N(R^{10})_2$, or $C_2$–$C_6$ alkenyl, and c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^3$ is selected from H and $CH_3$;

$R^2$ is selected from: H;

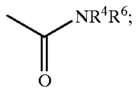

or $C_{1-5}$ alkyl, unbranched or branched, unsubstituted or substituted with one or more of:

1) aryl, 2) heterocycle,

3) $OR^4$,

4) $SR^5$, $SO_2R^5$, or

5)

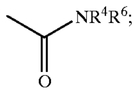

and $R^2$ and $R^3$ are optionally attached to the same carbon atom;

$R^4$ and $R^6$ are independently selected from:

H, $C_{1-4}$ alkyl, $C_{3-6}$ cycloalkyl, aryl, heterocycle, unsubstituted or substituted with:

a) $C_{1-4}$ alkoxy, b) halogen, or c) aryl or heterocycle;

$R^5$ is selected from:

$C_{1-4}$ alkyl or $C_{3-6}$ cycloalkyl, unsubstituted or substituted with:

a) $C_{1-4}$ alkoxy, b) halogen, or c) aryl or heterocycle;

$R^8$ is independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}OC(O)NR^{10}$—, and c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}$ OC(O) $NR^{10}$—;

$R^{9a}$ and $R^{9b}$ are independently selected from hydrogen, ethyl, cyclopropyl or methyl;

$R^{10}$ is independently selected from hydrogen, $C_1$–$C_{14}$ alkyl, substituted or unsubstituted benzyl and substituted or unsubstituted aryl;

$R^{11}$ is independently selected from $C_1$–$C_6$ alkyl and substituted or unsubstituted aryl;

$A^1$ is selected from: a bond, —C(O)—, O, —$N(R^{10})$—, or $S(O)_m$;

$A^3$ is selected from:

a) a bond, b) unsubstituted or substituted aryl, and c) unsubstituted or substituted heteroaryl;

X is selected from a bond, —$CH_2$—, —C(=O)—, or —$S(=O)_m$;

$G^1$ and $G^2$ are independently selected from: O or $H_2$;

Y is selected from: a bond O;

Z is an unsubstituted or substituted aryl, wherein the substituted aryl is substituted with one or more of the following:

a) $C_{1-4}$ alkyl, unsubstituted or substituted with:

1) $C_{1-4}$ alkoxy,

2) $NR^4R^6$,

3) $C_{3-6}$ cycloalkyl, 4) unsubstituted or substituted aryl, 5) heterocycle,

6) HO,

7) —$S(O)_mR^5$, or

8) —$C(O)NR^4R^6$, b) aryl or heterocycle, c) halogen, d) $OR^4$, e) $NR^4R^6$, f) CN, g) $NO_2$, h) $CF_3$, i) —$S(O)_mR^5$, j) —$C(O)NR^4R^6$, or k) $C_3$–$C_6$ cycloalkyl;

m is 0, 1 or 2;

n is 0 or 1; provided that n is not 0 if $A^1$ is a bond, O, —$N(R^{10})$— or $S(O)_m$;

p is 0, 1, 2, 3 or 4; and r is 0, 1, 2, 3, 4, or 5;

or the pharmaceutically acceptable salts thereof.

6. The compound according to claim 4 of Formula F:

F

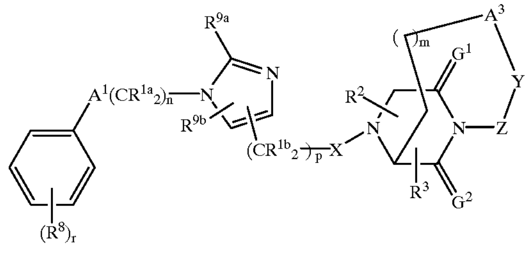

wherein:

$R^{1a}$ is selected from: hydrogen, $C_3$–$C_{10}$ cycloalkyl or $C_1$–$C_6$ alkyl;

$R^{1b}$ is independently selected from:

a) hydrogen, b) aryl, heterocycle, $C_3$–$C_{10}$ cycloalkyl, $R^{10}O$—, —$N(R^{10})_2$, or $C_2$–$C_6$ alkenyl, and c) $C_1$–$C_6$ alkyl unsubstituted or substituted by aryl, heterocycle, $C_3$–$C_{10}$ cycloalkyl, $C_2$–$C_6$ alkenyl, $R^{10}O$—, or —$N(R^{10})_2$;

$R^3$ is selected from H and $CH_3$;

$R^2$ is selected from: H;

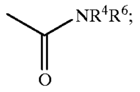

or $C_{1-5}$ alkyl, unbranched or branched, unsubstituted or substituted with one or more of:

1) aryl, 2) heterocycle,

3) $OR^4$,

4) $SR^5$, $SO_2R^5$, or

5)

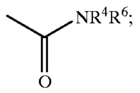

and $R^2$ and $R^3$ are optionally attached to the same carbon atom;

$R^4$ and $R^6$ are independently selected from:

H, $C_{1-4}$ alkyl, $C_{3-6}$ cycloalkyl, aryl, heterocycle, unsubstituted or substituted with:

a) $C_{1-4}$ alkoxy, b) halogen, or c) aryl or heterocycle;

$R^5$ is selected from:

$C_{1-4}$ alkyl or $C_{3-6}$ cycloalkyl, unsubstituted or substituted with:

a) $C_{1-4}$ alkoxy, b) halogen, or c) aryl or heterocycle;

$R^8$ is independently selected from:

a) hydrogen, b) $C_1$–$C_6$ alkyl, $C_2$–$C_6$ alkenyl, $C_2$–$C_6$ alkynyl, $C_1$–$C_6$ perfluoroalkyl, F, Cl, $R^{10}O$—, $R^{10}C(O)NR^{10}$—, CN, $NO_2$, $(R^{10})_2N$—$C(NR^{10})$—, $R^{10}C(O)$—, $R^{10}OC(O)$—, —$N(R^{10})_2$, or $R^{11}$ $OC(O)NR^{10}$—, and c) $C_1$–$C_6$ alkyl substituted by $C_1$–$C_6$ perfluoroalkyl, $R^{10}O$—, $R^{10}C(O)NR^{10}$—, $(R^{10})_2N$—$C(NR^{10})$—, $R^{10}C(O)$—, $R^{10}OC(O)$—, —$N(R^{10})_2$, or $R^{11}OC(O)NR^{10}$—;

$R^{9a}$ and $R^{9b}$ are independently selected from hydrogen, ethyl, cyclopropyl or methyl;

$R^{10}$ is independently selected from hydrogen, $C_1$–$C_{14}$ alkyl, substituted or unsubstituted benzyl and substituted or unsubstituted aryl;

$R^{11}$ is independently selected from $C_1$–$C_6$ alkyl and substituted or unsubstituted aryl;

$A^1$ is selected from: a bond, —C(O)—, O, —$N(R^{10})$—, or $S(O)_m$;

$A^3$ is selected from:

a) a bond, b) unsubstituted or substituted aryl, and c) unsubstituted or substituted heteroaryl;

$G^1$ and $G^2$ are independently selected from: O or $H_2$;

X is selected from a bond, —$CH_2$—, —C(=O)—, or —$S(=O)_m$;

Y is selected from: a bond O;

Z is an unsubstituted or substituted aryl, wherein the substituted aryl is substituted with one or more of the following:

a) $C_{1-4}$ alkyl, unsubstituted or substituted with:

1) $C_{1-4}$ alkoxy,

2) $NR^4R^6$,

3) $C_{3-6}$ cycloalkyl, 4) unsubstituted or substituted aryl, 5) heterocycle,

6) HO,

7) —$S(O)_mR^5$, or

8) —$C(O)NR^4R^6$, b) aryl or heterocycle, c) halogen, d) $OR^4$, e) $NR^4R^6$, f) CN, g) $NO_2$, h) $CF_3$, i) —$S(O)_mR^5$, j) —$C(O)NR^4R^6$, or k) $C_3$–$C_6$ cycloalkyl;

m is 0, 1 or 2;

n is 0 or 1; provided that n is not 0 if $A^1$ is a bond, O, —$N(R^{10})$— or $S(O)_m$;

p is 0, 1, 2, 3 or 4; and r is 0, 1, 2, 3, 4 or 5;

or the pharmaceutically acceptable salts thereof.

7. A compound which inhibits farnesyl-protein transferase which is:

1(R),5(S)-3-[(3-trifluoromethyl)phenyl]-8-[(4-cyanobenzyl)-5-imidazolylmethyl]-3,8-diaza-2-oxobicyclo[3.2.1]octane (±)-9-[1-(4-cyanobenzyl)-5-imidazolylmethyl]-b-benzo-1,9-diaza-4-oxa-12-oxobicyclo[6.3.1]dodecane (±)-9-[1-(4-cyanobenzyl)-5-imidazolylmethyl]-1,9-diaza-b,e-dibenzo-4-oxa-12-oxobicyclo[6.3.1]dodecane (±)-9-[1-(4-cyanobenzyl)-5-imidazolylcarbonyl]-1,9-diaza-b,e-dibenzo-4-oxa-bicyclo[6.3.1]dodecane or a pharmaceutically acceptable salt or optical isomer thereof.

8. The compound according to claim 7 which is:

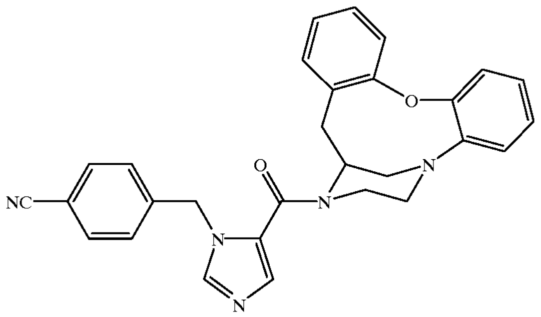

(±)-9-[1-(4-cyanobenzyl)-5-imidazolylcarbonyl]-1,9-diaza-b,e-dibenzo-4-oxa-bicyclo [6.3.1]dodecane or a pharmaceutically acceptable salt or optical isomer thereof.

9. The compound according to claim 7 which is:

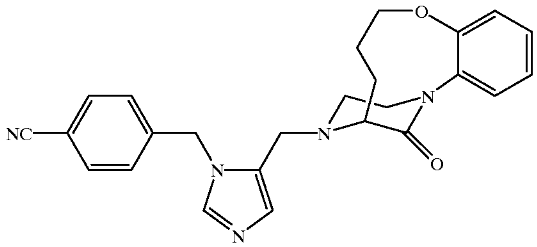

(±)-9-[1-(4-cyanobenzyl)-5-imidazolylmethyl]-b-benzo-1,9-diaza-4-oxa-12-Oxobicyclo[6.3.1]dodecane or a pharmaceutically acceptable salt or optical isomer thereof.

10. The compound according to claim 7 which is:

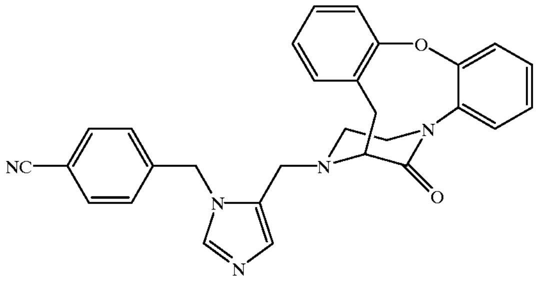

(±)-9-[1-(4-cyanobenzyl)-5-imidazolylmethyl]-1,9-diaza-b,e-dibenzo-4-oxa-12-oxobicyclo[6.3.1]dodecane or a pharmaceutically acceptable salt or optical isomer thereof.

11. A compound according to claim 7 which is:

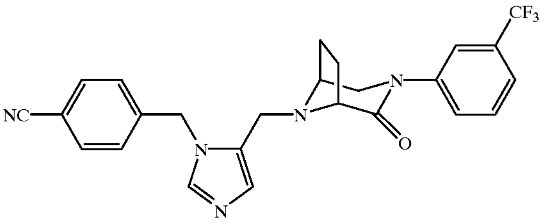

1(R),5(S)-3-[(3-trifluoromethyl)phenyl]-8-[(4-cyanobenzyl)-5-imidazolylmethyl]-3,8-diaza-2-oxobicyclo[3.2.1]octane or a pharmaceutically acceptable salt or optical isomer thereof.

12. A pharmaceutical composition comprising a pharmaceutical carrier, and dispersed therein, a therapeutically effective amount of a compound of claim 1.

13. A pharmaceutical composition comprising a pharmaceutical carrier, and dispersed therein, a therapeutically effective amount of a compound of claim 2.

14. A pharmaceutical composition comprising a pharmaceutical carrier, and dispersed therein, a therapeutically effective amount of a compound of claim 7.

15. A method for inhibiting farnesyl-protein transferase which comprises administering to a mammal in need thereof a therapeutically effective amount of a composition of claim 12.

16. A method for inhibiting farnesyl-protein transferase which comprises administering to a mammal in need thereof a therapeutically effective amount of a composition of claim 13.

17. A method for inhibiting farnesyl-protein transferase which comprises administering to a mammal in need thereof a therapeutically effective amount of a composition of claim 14.

18. A method for treating cancer which comprises administering to a mammal in need thereof a therapeutically effective amount of a composition of claim 12.

19. A method for treating cancer which comprises administering to a mammal in need thereof a therapeutically effective amount of a composition of claim 13.

20. A method for treating cancer which comprises administering to a mammal in need thereof a therapeutically effective amount of a composition of claim 14.

21. A method for treating neurofibromin benign proliferative disorder which comprises administering to a mammal in need thereof a therapeutically effective amount of a compound of claim 1.

22. A method for treating blindness related to retinal vascularization which comprises administering to a mammal in need thereof a therapeutically effective amount of a compound of claim 1.

23. A method for treating infections from hepatitis delta and related viruses which comprises administering to a mammal in need thereof a therapeutically effective amount of a compound of claim 1.

24. A method for preventing restenosis which comprises administering to a mammal in need thereof a therapeutically effective amount of a compound of claim 1.

25. A method for treating polycystic kidney disease which comprises administering to a mammal in need thereof a therapeutically effective amount of a compound of claim 1.

26. A method for treating neurofibromin benign proliferative disorder which comprises administering to a mammal in need thereof a therapeutically effective amount of a compound of claim 2.

27. A method for treating blindness related to retinal vascularization which comprises administering to a mammal in need thereof a therapeutically effective amount of a compound of claim 2.

28. A method for treating infections from hepatitis delta and related viruses which comprises administering to a mammal in need thereof a therapeutically effective amount of a compound of claim 2.

29. A method for preventing restenosis which comprises administering to a mammal in need thereof a therapeutically effective amount of a compound of claim 2.

30. A method for treating polycystic kidney disease which comprises administering to a mammal in need thereof a therapeutically effective amount of a compound of claim 2.

31. A pharmaceutical composition made by combining the compound of claim 1 and a pharmaceutically acceptable carrier.

32. A process for making a pharmaceutical composition comprising combining a compound of claim 1 and a pharmaceutically acceptable carrier.

33. A pharmaceutical composition made by combining the compound of claim 2 and a pharmaceutically acceptable carrier.

34. A process for making a pharmaceutical composition comprising combining a compound of claim 2 and a pharmaceutically acceptable carrier.

* * * * *

UNITED STATES PATENT AND TRADEMARK OFFICE
CERTIFICATE OF CORRECTION

PATENT NO. : 6,103,723
DATED : August 15, 2000
INVENTOR(S) : Jeffrey M. Bergman, Christopher J. Dinsmore, Samuel L. Graham It is certified that error appears in the above-identified patent and that said Letters Patent is hereby corrected as shown below:

Title page,
The "*Attorney, Agent, or Firm*" should read as follows: -- Dianne Pecoraro; Mark R. Daniel --.

Column 73, claim 3,
Line 22, should read as follows:
-- c) $C_1$-$C_6$) alkyl unsubstituted or substituted by aryl,--.

Column 74, claim 3,
Line 30, should read as follows: -- Y is selected from: a bond or O; --.

Column 75, claim 4,
Line 36 should read follows: -- or $C_{1-5}$ alkyl, unbranched or branched, unsubstitued --.

Column 76, claim 4,
line 31, should read as follows: -- Y is selected from a bond or O; --.

Signed and Sealed this

Twenty-third Day of October, 2001

*Attest:*

NICHOLAS P. GODICI

*Attesting Officer* *Acting Director of the United States Patent and Trademark Office*